US008798283B2

(12) United States Patent
Gauger, Jr. et al.

(10) Patent No.: US 8,798,283 B2
(45) **Date of Patent: *Aug. 5, 2014**

(54) PROVIDING AMBIENT NATURALNESS IN ANR HEADPHONES

(71) Applicants: Daniel M. Gauger, Jr., Berlin, MA (US); Ricardo F. Carreras, Southborough, MA (US); Jason Harlow, Watertown, MA (US); Neil Adam Ranney, Boston, MA (US); Martin David Ring, Ashland, MA (US); Roman Sapiejewski, Boston, MA (US); Vishu Singh, Brighton, MA (US)

(72) Inventors: Daniel M. Gauger, Jr., Berlin, MA (US); Ricardo F. Carreras, Southborough, MA (US); Jason Harlow, Watertown, MA (US); Neil Adam Ranney, Boston, MA (US); Martin David Ring, Ashland, MA (US); Roman Sapiejewski, Boston, MA (US); Vishu Singh, Brighton, MA (US)

(73) Assignee: Bose Corporation, Framingham, MA (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/667,103

(22) Filed: Nov. 2, 2012

(65) Prior Publication Data

US 2014/0126734 A1 May 8, 2014

(51) Int. Cl.
*A61F 11/06* (2006.01)
*H03B 29/00* (2006.01)

(52) U.S. Cl.
USPC .......... 381/71.6

(58) Field of Classification Search
USPC .......... 381/71.1, 71.6, 72
See application file for complete search history.

(56) References Cited

U.S. PATENT DOCUMENTS

| | | | | |
|---|---|---|---|---|
| 5,325,436 | A | 6/1994 | Soli et al. | |
| 6,567,524 | B1 | 5/2003 | Svean et al. | |
| 7,039,195 | B1 | 5/2006 | Svean et al. | |
| 8,073,150 | B2 | 12/2011 | Joho et al. | |
| 8,189,803 | B2 | 5/2012 | Bergeron et al. | |
| 8,208,650 | B2 | 6/2012 | Joho et al. | |
| 8,280,066 | B2 * | 10/2012 | Joho et al. | 381/71.6 |
| 2001/0046304 | A1 | 11/2001 | Rast | |
| 2002/0141599 | A1 | 10/2002 | Trajkovic et al. | |
| 2007/0253569 | A1 | 11/2007 | Bose | |
| 2008/0089530 | A1 | 4/2008 | Bostick et al. | |
| 2008/0298600 | A1 | 12/2008 | Poe et al. | |
| 2009/0147969 | A1 | 6/2009 | Kinouchi et al. | |
| 2009/0310805 | A1 | 12/2009 | Petroff | |

(Continued)

FOREIGN PATENT DOCUMENTS

| | | | |
|---|---|---|---|
| EP | 2104374 | A1 | 9/2009 |
| EP | 2131354 | A2 | 12/2009 |

(Continued)

OTHER PUBLICATIONS

Invitation to Pay Additional Fees dated Jan. 8, 2014 for International application No. PCT/US2013067717.

(Continued)

*Primary Examiner* — Ping Lee

(57) ABSTRACT

In an active noise reducing headphone, a signal processor applies filters and control gains of both the feed-forward and feedback active noise cancellation signal paths. The signal processor is configured to apply first feed-forward filters to the feed-forward signal path and apply first feedback filters to the feedback signal path during a first operating mode providing effective cancellation of ambient sound, and to apply second feed-forward filters to the feed-forward signal path during a second operating mode providing active hear-through of ambient sounds with ambient naturalness.

32 Claims, 8 Drawing Sheets

(56) References Cited

U.S. PATENT DOCUMENTS

| | | | | |
|---|---|---|---|---|
| 2009/0323976 | A1 | 12/2009 | Asada et al. | |
| 2010/0002896 | A1 | 1/2010 | Arndt et al. | |
| 2010/0296668 | A1 | 11/2010 | Lee et al. | |
| 2011/0038496 | A1 * | 2/2011 | Lott et al. | 381/309 |
| 2011/0158419 | A1 | 6/2011 | Theverapperuma et al. | |
| 2011/0299692 | A1 | 12/2011 | Rung et al. | |
| 2012/0063611 | A1 * | 3/2012 | Kimura | 381/71.6 |
| 2012/0250873 | A1 | 10/2012 | Bakalos et al. | |

FOREIGN PATENT DOCUMENTS

| | | | |
|---|---|---|---|
| EP | 2217005 | A1 | 8/2010 |
| EP | 2228902 | A1 | 9/2010 |
| WO | 9423419 | A1 | 10/1994 |
| WO | 2008137870 | A1 | 11/2008 |
| WO | 2009043550 | A1 | 4/2009 |
| WO | 2011020992 | A2 | 2/2011 |
| WO | 2011118595 | A1 | 9/2011 |
| WO | 2012071650 | A1 | 6/2012 |

OTHER PUBLICATIONS

International Search Report and Written Opinion dated Apr. 3, 2014 for International application No. PCT/US2013/067712.

International Search Report and Written Opinion dated Apr. 2, 2014 for International application No. PCT/US2013/067389.

International Search Report and Written Opinion dated Mar. 7, 2014 for International application No. PCT/US2013/067717.

"TLV320AIC3101 Low-Power Stereo Audio Codec for Portable Audio/Telephony" Dec. 2008, XP055056392, Retrieved from the Internet URL: www.ti.com/lit/ds/symlink/tlv320aic3101.pdf [retrieved on Mar. 13, 2013] pp. 1-3, 40-pp. 45, 78.

"Harman Kardon CL Headphones, Are One of Five New Headphones From Harman Kardon", thestreet.com Press Releases, Jun. 12, 2012, XP055056401, Retrieved from the Internet URL: http://www.thestreet.com/print/story/11577477.html [retrieved on Mar. 13, 2013].

Invitation to Pay Additional Fees dated Jan. 30, 2014 for International application No. PCT/US2013/067712.

Invitation to Pay Additional Fees dated Feb. 5, 2014 for International application No. PCT/US2013/067389.

* cited by examiner

PROVIDING AMBIENT NATURALNESS IN ANR HEADPHONES

BACKGROUND

This disclosure relates to providing natural hear-through in active noise reducing (ANR) headphones, reproducing audio signals simultaneously with hear-through in ANR headphones, and eliminating the occlusion effect in ANR headphones.

Noise reducing headphones are used to block ambient noise from reaching the ear of a user. Noise reducing headphones may be active, i.e., ANR headphones, in which electronic circuits are used to generate anti-noise signals that destructively interfere with ambient sound to cancel it, or they may be passive, in which the headphones physically block and attenuate ambient sound. Most active headphones also include passive noise reduction measures. Headphones used for communications or for listening to entertainment audio may include either or both active and passive noise reduction capabilities. ANR headphones may use the same speakers for audio (by which we include both communications and entertainment) and cancellation, or they may have separate speakers for each.

Some headphones offer a feature commonly called "talk-through" or "monitor," in which external microphones are used to detect external sounds that the user might want to hear. Those sounds are reproduced by speakers inside the headphones. In ANR headphones with a talk-through feature, the speakers used for talk-through may be the same speakers used for noise cancellation, or they may be additional speakers. The external microphones may also be used for feed-forward active noise cancellation, for picking up the user's own voice for communications purposes, or they may be dedicated to providing talk-through. Typical talk-through systems apply only minimal signal processing to the external signal, and we refer to these as "direct talk-through" systems. Sometimes direct talk-through systems use a band-pass filter to restrict the external sounds to voice-band or some other band of interest. The direct talk-through feature may be manually triggered or may be triggered by detection of a sound of interest, such as voice or an alarm.

Some ANR headphones include a feature to temporarily mute the noise cancellation so that the user can hear the environment, but they do not simultaneously provide talk-through, rather, they rely on enough sound passively passing through the headphones to make the environment audible. We refer to this feature as passive monitoring.

SUMMARY

In general, in some aspects, an active noise reducing headphone includes an ear cup configured to couple to a wearer's ear to define an acoustic volume including the volume of air within the wearer's ear canal and a volume within the ear cup, a feed-forward microphone acoustically coupled to an external environment and electrically coupled to a feed-forward active noise cancellation signal path, a feedback microphone acoustically coupled to the acoustic volume and electrically coupled to a feedback active noise cancellation signal path, an output transducer acoustically coupled to the acoustic volume via the volume within the ear cup and electrically coupled to both the feed-forward and feedback active noise cancellation signal paths, and a signal processor configured to apply filters and control gains of both the feed-forward and feedback active noise cancellation signal paths. The signal processor is configured to apply first feed-forward filters to the feed-forward signal path and apply first feedback filters to the feedback signal path during a first operating mode providing effective cancellation of ambient sound, and to apply second feed-forward filters to the feed-forward signal path during a second operating mode providing active hear-through of ambient sounds with ambient naturalness.

Implementations may include one or more of the following. The second feed-forward filters may cause the headphone to have a total system response at the wearer's ear that may be smooth and piecewise linear. The difference in the overall noise reduction in speech noise between the first operating mode and the second operating mode may be at least 12 dBA. The second feed-forward filters may have value $K_{ht}$ selected to cause the formula $$\frac{G_{pfb}}{G_{oea}} + \frac{K_{ht} * G_{nx} * G_{ffe}}{G_{oea}}$$

to be approximately equal to a predetermined target value. The signal processor may be further configured to apply second feedback filters different from the first feedback filters to the feedback signal path during the second operating mode. The feedback signal path and the ear cup in combination may reduce ambient noise reaching the entrance to the ear canal by at least 8 dB at all frequencies between 100 Hz and 10 kHz. The feedback signal path may be operative over a frequency range extending higher than 500 Hz. The second feed-forward filters may cause the total system response to be smooth and piecewise linear in a region extending to frequencies above 3 kHz. The second feed-forward filters may cause the total system response to be smooth and piecewise linear in a region extending to frequencies below 300 Hz. The feedback signal path may be implemented in a digital signal processor and may have a latency less than 250 μs. The second feed-forward filter defines non-minimum phase zeros in a transfer function characterizing the feed-forward signal path.

The signal processor may be further configured to apply third feed-forward filters to the feed-forward signal path during a third operating mode providing active hear-through of ambient sounds with a different total response than may be provided in the second operating mode. A user input may be provided, with the signal processor configured to select between the first, second, or third feed-forward filters based on the user input. The user input may include a volume control. The signal processor may be configured to select between the second and third feed-forward filters automatically. The signal processor may be configured to select between the second and third feed-forward filters based on a time-average measurement of the level of the ambient noise. The signal processor may be configured to make the selection between the second and third feed-forward filters upon receipt of a user input calling for activation of a hear-through mode. The signal processor may be configured to make the selection between the second and third feed-forward filters periodically.

The signal processor may be a first signal processor and the feed-forward signal path may be a first feed-forward signal path, with the headphone including a second ear cup configured to couple to a wearer's second ear to define a second acoustic volume comprising the volume of air within the wearer's second ear canal and a volume within the second ear cup, a second feed-forward microphone acoustically coupled to an external environment and electrically coupled to a second feed-forward active noise cancellation signal path, a second feedback microphone acoustically coupled to the second acoustic volume and electrically coupled to a second feedback active noise cancellation signal path, a second output transducer acoustically coupled to the second acoustic volume via the volume within the second ear cup and electrically coupled to both the second feed-forward and second feedback active noise cancellation signal paths, and a second signal processor configured to apply filters and control gains of both the second feed-forward and second feedback active noise cancellation signal paths. The second signal processor may be configured to apply third feed-forward filters to the second feed-forward signal path and apply the first feedback filters to the second feedback signal path during the first operating mode of the first signal processor, and to apply fourth feed-forward filters to the second feed-forward signal path during the second operating mode of the first signal processor. The first and second signal processors may be portions of a single signal processing device. The third feed-forward filters may not be identical to the first feed-forward filters. Only one of the first or second signal processor may apply the respective second or fourth feed-forward filters to the corresponding first or second feed-forward signal path during a third operating mode. The third operating mode may be activated in response to a user input.

The first signal processor may be configured to receive a crossover signal from the second feed-forward microphone, apply fifth feed-forward filters to the crossover signal, and insert the filtered crossover signal into the first feed-forward signal path. The signal processor may be configured to apply a single-channel noise reduction filter to the first feed-forward signal path during the second operating mode. The signal processor may be configured to detect high-frequency signals in the feed-forward signal path, compare the amplitude of the detected high-frequency signals to a threshold indicative of a positive feedback loop, and, if the amplitude of the detected high-frequency signals is higher than the threshold, activate a compressing limiter. The signal processor may be configured to decrease an amount of compression applied by the limiter gradually when the amplitude of the detected high-frequency signals is no longer higher than the threshold, and, if the amplitude of the detected high-frequency signals returns to a level higher than the threshold after reducing the amount of compression, increase the amount of compression to the lowest level at which the amplitude of the detected high-frequency signals remain below the threshold. The signal processor may be configured to detect the high-frequency signals using a phase-locked loop monitoring a signal in the feed-forward signal path.

The ear cup may provide a volume enclosing the feed-forward microphone, with a screen covering an aperture between the volume enclosing the feed-forward microphone and the external environment. The aperture between the volume enclosing the feed-forward microphone and the external environment may be at least 10 $mm^2$. The aperture between the volume enclosing the feed-forward microphone and the external environment may be at least 20 $mm^2$. The screen and the feed-forward microphone may be separated by a distance of at least 1.5 mm.

In general, in one aspect, an active noise reducing headphone includes an ear cup configured to couple to a wearer's ear to define an acoustic volume including the volume of air within the wearer's ear canal and a volume within the ear cup, a feedback microphone acoustically coupled to the acoustic volume and electrically coupled to a feedback active noise cancellation signal path, an output transducer acoustically coupled to the acoustic volume via the first volume and electrically coupled to the feedback signal path, and a signal processor configured to apply filters and control gains of the feedback signal path. The signal processor is configured to apply first feedback filters to the feedback signal path, the first feedback filters causing the feedback signal path to operate at a first gain level, as a function of frequency, during a first operating mode, and apply second feedback filters to the feedback signal path, the second feedback filters causing the feedback signal path to operate at a second gain level less than the first gain level at some frequencies during a second operating mode, the first gain level being a level of gain that results in effective cancellation of sounds transmitted through or around the ear cup and through the user's head into the acoustic volume when the ear cup is coupled to the wearer's ear, and the second level being a level of gain that is matched to the level of sound of a typical wearer's voice transmitted through the wearer's head when the ear cup is coupled to the wearer's ear.

Implementations may include one or more of the following. A feed-forward microphone may be acoustically coupled to an external environment and electrically coupled to a feed-forward active noise cancellation signal path, with the output transducer electrically coupled to the feed-forward signal path and the signal processor configured to apply filters and control gains of the feed-forward signal path. In the first operating mode the signal processor may be configured to apply first feed-forward filters to the feed-forward signal path in conjunction with applying the first feedback filters to the feedback signal path to achieve effective cancellation of ambient sound, and in the second operating mode, the signal processor may be configured to apply second feed-forward filters to the feed-forward signal path, the second filters being selected to provide active hear-through of ambient sounds with ambient naturalness. The second feedback filters and the second feed-forward filters may be selected to provide active hear-through of a user's own voice with self-naturalness. The second feed-forward filters applied to the feed-forward path may be a non-minimum phase response. The sound of the typical wearer's voice below a first frequency passively transmitted through the wearer's head may be amplified when the ear cup is coupled to the wearer's ear, and sound above the first frequency may be attenuated when the ear cup is so coupled, with the feedback signal path operative over a frequency range extending higher than the first frequency.

The signal processor may be a first signal processor and the feedback signal path may be a first feedback signal path, with the headphone including a second ear cup configured to couple to a wearer's second ear to define a second acoustic volume comprising the volume of air within the wearer's second ear canal and a volume within the second ear cup, a second feedback microphone acoustically coupled to the second acoustic volume and electrically coupled to a second feedback active noise cancellation signal path, a second output transducer acoustically coupled to the second acoustic volume via the volume within the second ear cup and electrically coupled to both the second feedback active noise cancellation signal path, and a second signal processor configured to apply filters and control gains of the second feedback active noise cancellation signal path. The second signal processor may be configured to apply third feedback filters to the second feedback signal path, the second feedback filters causing the second feedback signal path to operate at the first gain level during the first operating mode of the first signal processor, and to apply fourth feedback filters to the second feedback signal path to operate at the second gain level during the second operating mode of the first signal processor. The first and second signal processors may be portions of a single signal processing device. The third feedback filters may not be identical to the first feedback filters.

In general, in one aspect, a method is described for configuring an active noise reducing headphone that includes an ear cup configured to couple to a wearer's ear to define an acoustic volume including the volume of air within the wearer's ear canal and a volume within the ear cup, a feed-forward microphone acoustically coupled to an external environment and electrically coupled to a feed-forward active noise cancellation signal path, a feedback microphone acoustically coupled to the acoustic volume and electrically coupled to a feedback active noise cancellation signal path, an output transducer acoustically coupled to the acoustic volume via the volume within the ear cup and electrically coupled to both the feed-forward and feedback active noise cancellation signal paths, and a signal processor configured to apply filters and control gains of both the feed-forward and feedback active noise cancellation signal paths. The method includes, for at least one frequency, measuring the ratio $$\frac{|G_{cev}|}{|G_{oev}|}$$

with the active noise reduction circuit of the headphones inactive, where $G_{cev}$ is the response at a user's ear to environmental noise when the headphones are worn, and $G_{oev}$ is the response at the user's ear to environmental noise when the headphones are not present, selecting a filter $K_{on}$ for the feedback path having a magnitude that results in the feedback loop having a desensitivity equal to the determined ratio at the at least one frequency; selecting a filter $K_{ht}$ for the feed-forward signal path that will provide ambient naturalness; applying the selective filters $K_{on}$ and $K_{ht}$ to the feedback path and feed-forward path, respectively; at the at least one frequency, measuring the ratio $$\frac{|G_{cev}|}{|G_{oev}|}$$

with the active noise reduction circuit of the headphones active; and modifying the phase of $K_{ht}$ without altering the magnitude thereof to minimize deviation of the measured value of $$\frac{|G_{cev}|}{|G_{oev}|}$$

from unity.

Implementations may include one or more of the following. The steps of selecting $K_{on}$ and $K_{ht}$, applying the selected filters, and measuring the ratio $$\frac{|G_{cev}|}{|G_{oev}|}$$

may be iterated, and the phase of $K_{ht}$ further adjusted, until a target balance of ambient response and own-voice response is reached. Selecting the filter for the feed-forward signal path may include selecting a value of $K_{ht}$ that causes the formula $$\frac{G_{pfb}}{G_{oea}}+\frac{K_{ht}*G_{nx}*G_{ffe}}{G_{oea}}$$

to be approximately equal to a predetermined target value.

In general, in one aspect, an active noise reducing headphone includes an ear cup configured to couple to a wearer's ear to define an acoustic volume comprising the volume of air within the wearer's ear canal and a volume within the ear cup, a feed-forward microphone acoustically coupled to an external environment and electrically coupled to a feed-forward active noise cancellation signal path, a feedback microphone acoustically coupled to the acoustic volume and electrically coupled to a feedback active noise cancellation signal path, a signal input for receiving an input electronic audio signal and electrically coupled to an audio playback signal path, an output transducer acoustically coupled to the acoustic volume via the volume within the ear cup and electrically coupled to the feed-forward and feedback active noise cancellation signal paths and the audio playback signal path, and a signal processor configured to apply filters and control gains of both the feed-forward and feedback active noise cancellation signal paths. The signal processor is configured to apply first feed-forward filters to the feed-forward signal path and apply first feedback filters to the feedback signal path during a first operating mode providing effective cancellation of ambient sound, apply second feed-forward filters to the feed-forward signal path during a second operating mode providing active hear-through of ambient sounds with ambient naturalness, and provide the input electronic audio signal to the output transducer via the audio playback signal path during both the first and second operating modes.

Implementation may include one or more of the following. The residual sound at the ear due to external noise present in the headphones during the first operating mode may be 12 dBA less than the residual sound at the ear due to the same external noise present in the headphones during the second operating mode. The total audio level of the headphone in reproducing the input audio signal may be the same in both the first and the second operating modes. The frequency response of the headphone may be the same in both the first and the second operating modes, and the signal processor may be configured to vary a gain applied to the audio playback signal path between the first and the second operating modes. The signal processor may be configured to decrease the gain applied to the audio playback signal path during the second operating mode relative to the gain applied to the audio playback signal path during the first operating mode. The signal processor may be configured to increase the gain applied to the audio playback signal path during the second operating mode relative to the gain applied to the audio playback signal path during the first operating mode.

The headphone may include a user input, with the signal processor configured to apply the second feed-forward filters to the feed-forward signal path during a third operating mode providing active hear-through of ambient sounds with ambient naturalness, not provide the input electronic audio signal to the output transducer via the audio playback signal path during the third operating mode, and upon receiving a signal from the user input during the first operating mode, transition to a selected one of the second operating mode or third operating mode. The selection of whether to transition to the second operating mode or the third operating mode may be based on a duration of time over which the signal is received from the user input. The selection of whether to transition to the second operating mode or the third operating mode may be based on a pre-determined configuration setting of the headphone. The pre-determined configuration setting of the headphone may be determined by the position of a switch. The pre-determined configuration setting of the headphone may be determined by instructions received by the headphone from a computing device. The signal processor may be configured to stop providing the input electronic audio signal by transmitting a command to a source of the input electronic audio signal to pause playback of a media source upon entering the third processing mode.

The audio playback signal path and output transducer may be operational when no power is applied to the signal processor. The signal processor may also be configured to disconnect the audio playback signal path from the output transducer upon activation of the signal processor, and reconnect the audio playback signal path to the output transducer via filters applied by the signal processor after a delay. The signal processor may also be configured to initially maintain the audio playback signal path to the output transducer upon activation of the signal processor, and after a delay, disconnect the audio playback signal path from the output transducer and simultaneously connect the audio playback signal path to the output transducer via filters applied by the signal processor. The total audio response of the headphone in reproducing the input audio signal when the signal processor is not active may be characterized by a first response, and the signal processor may be configured to, after the delay, apply first equalizing filters that result in the total audio response of the headphone in reproducing the input audio signal to remain the same as the first response, and after a second delay, apply second equalizing filters that result in a different total audio response than the first response.

In general, in one aspect, an active noise reducing headphone has an active noise-cancelling mode and an active hear-through mode, and the headphone changes between the active noise-cancelling mode and the active hear-through mode based on detection of a user touching a housing of the headphone. In general, in another aspect, an active noise reducing headphone has an active noise-cancelling mode and an active hear-through mode, and the headphone changes between the active noise-cancelling mode and the active hear-through mode based on a command signal received from an external device.

Implementations may include one or more of the following. An optical detector may be used for receiving the command signal. A radio-frequency receiver may be used for receiving the command signal. The command signal may include an audio signal. The headphone may be configured to receive the command signal through a microphone integrated into the headphone. The headphone may be configured to receive the command signal through a signal input of the headphone for receiving an input electronic audio signal.

In general, in one aspect, an active noise reducing headphone includes an ear cup configured to couple to a wearer's ear to define an acoustic volume comprising the volume of air within the wearer's ear canal and a volume within the ear cup, a feed-forward microphone acoustically coupled to an external environment and electrically coupled to a feed-forward active noise cancellation signal path, a feedback microphone acoustically coupled to the acoustic volume and electrically coupled to a feedback active noise cancellation signal path, an output transducer acoustically coupled to the acoustic volume via the volume within the ear cup and electrically coupled both to the feed-forward and feedback active noise cancellation signal paths, and a signal processor configured to apply filters and control gains of both the feed-forward and feedback active noise cancellation signal paths. The signal processor is configured to operate the headphone in a first operating mode providing effective cancellation of ambient sound and in a second operating mode providing active hear-through of ambient sounds, and change between the first and second operating modes based on a comparison of signals from the feed-forward microphone and the feedback microphone.

Implementations may include one or more of the following. The signal processor may be configured to change from the first operating mode to the second operating mode when the comparison of signals from the feed-forward microphone and the feedback microphone indicates that the user of the headphone is speaking. The signal processor may be further configured to change from the second operating mode to the first operating mode a pre-determined amount of time after the comparison of signals from the feed-forward microphone and the feedback microphone no longer indicates that the user of the headphone is speaking. The signal processor may be configured to change from the first operating mode to the second operating mode when signals from the feedback microphone are correlated with the signals from the feed-forward microphone within a frequency band consistent with the portion of human speech amplified by the occlusion effect and are above a threshold level indicative of the user speaking.

In general, in one aspect, an active noise reducing headphone has an active noise-cancelling mode and an active hear-through mode, and includes an indicator activated when the headphone is in the active hear-through mode, the indicator visible over a limited viewing angle viewable only from in front of the headphone. In general, in another aspect, an active noise reducing headphone includes an ear cup configured to couple to a wearer's ear to define an acoustic volume comprising the volume of air within the wearer's ear canal and a volume within the ear cup, a feed-forward microphone acoustically coupled to an external environment and electrically coupled to a feed-forward active noise cancellation signal path, a feedback microphone acoustically coupled to the acoustic volume and electrically coupled to a feedback active noise cancellation signal path, an output transducer acoustically coupled to the acoustic volume via the volume within the ear cup and electrically coupled both to the feed-forward and feedback active noise cancellation signal paths, and a signal processor configured to apply filters and control gains of both the feed-forward and feedback active noise cancellation signal paths. The signal processor is configured to operate the headphone in a first operating mode providing effective cancellation of ambient sound and in a second operating mode providing active hear-through of ambient sounds. During the second operating mode, the signal processor is configured to detect high-frequency signals in the feed-forward active noise cancellation signal path exceeding a threshold level indicative of abnormally high acoustic coupling of the output transducer to the feed-forward microphone, in response to the detection, apply a compressing limiter to the feed-forward signal path, and, once the high-frequency signals are no longer detected at levels above the threshold, remove the compressing limiter from the feed-forward signal path.

In general, in one aspect, an active noise reducing headphone has an active noise-cancelling mode and an active hear-through mode, and includes a right feed-forward microphone, a left feed-forward microphone, and a signal output for providing signals from the right and left feed-forward microphones to an external device. In general, in another aspect, a system for providing binaural telepresence includes a first communication device, a first set of active noise reducing headphones having an active noise-cancelling mode and an active hear-through mode, coupled to the first communication device and configured to provide first left and right feed-forward microphone signals to the first communication device, a second communication device capable of receiving signals from the first communication device, and a second set of active noise reducing headphones having an active noise-cancelling mode, coupled to the second communication device. The first communication device is configured to transmit the first left and right feed-forward microphone signals to the second communication device. The second communication device is configured to provide the first left and right feed-forward microphone signals to the second set of headphones. The second set of headphones are configured to activate their noise-cancelling mode while reproducing the first left and right feed-forward microphone signals so that a user of the second set of headphones hears ambient noise from the environment of the first set of headphones, and to filter the first left and right feed-forward microphone signals so that the user of the second set of headphones hears the ambient noise from the first set of headphones with ambient naturalness.

Implementations may include one or more of the following. The second set of headphones may be configured, in a first operating mode, to provide the first right feed-forward microphone signal to a left ear cup of the second set of headphones, and to provide the first left feed-forward microphone signal to a right ear cup of the second set of headphones. The second set of headphones may be configured, in a second operating mode, to provide the first right feed-forward microphone signal to a right ear cup of the second set of headphones, and to provide the first left feed-forward microphone signal to a left ear cup of the second set of headphones. The first and second communication devices may also be configured to provide visual communication between their users, and the second set of headphones may be configured to operate in the first operating mode when the visual communication is active, and to operate in the second operating mode when the visual communication is not active. The first communication device may be configured to record the first left and right feed-forward microphone signals. The second set of headphones may have an active hear-through mode, and be configured to provide second left and right feed-forward microphone signals to the second communication device, with the second communication device configured to transmit the second left and right feed-forward microphone signals to the first communication device, the first communication device configured to provide the second left and right feed-forward microphone signals to the first set of headphones, and the first set of headphones configured to activate their noise-cancelling mode while reproducing the second left and right feed-forward microphone signals so that a user of the first set of headphones hears ambient noise in the environment of the second set of headphones and filter the second left and right feed-forward microphone signals so that the user of the first set of headphones hears the ambient noise from the second set of headphones with ambient naturalness. The first and second communication devices may be configured to coordinate the operating modes of the first and second sets of headphones, so that the users of both sets of headphones hear the ambient noise in the environment of a selected one of the first and second sets of headphones, by placing the selected one of the first and second sets of headphones into its active hear-through mode, and placing the other set of headphones into its noise-cancelling mode while reproducing the feed-forward microphone signals from the selected set of headphones.

Advantages include providing ambient and self naturalness in headphones, allowing a user to enjoy audio content during an active hear-through mode, reducing the occlusion effect of headphones, and providing binaural telepresence.

Other features and advantages will be apparent from the description and the claims.

DESCRIPTION

Figure 1:
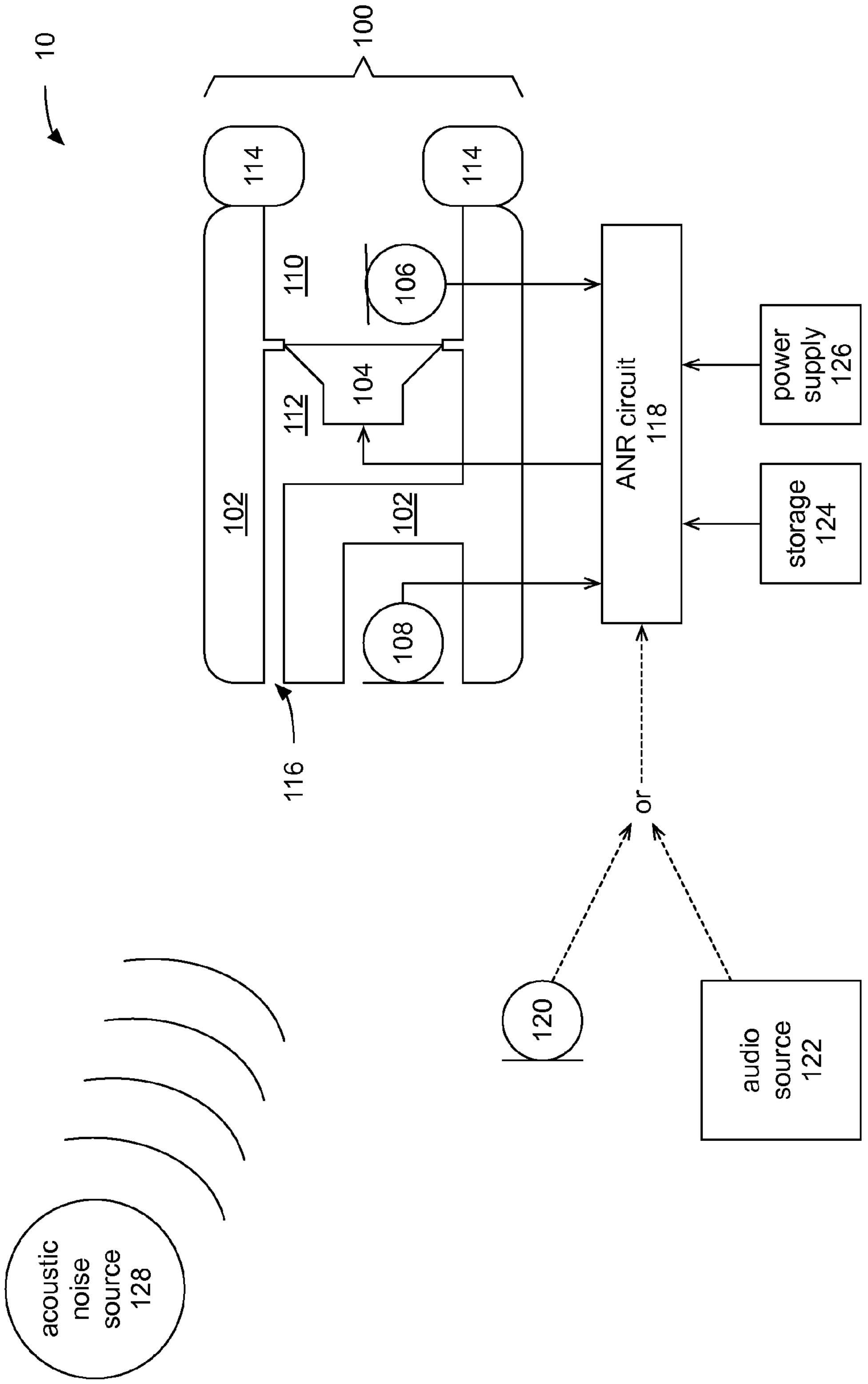
FIG. 1 shows a schematic diagram of an active noise reducing (ANR) headphone.

A typical active noise reduction (ANR) headphone system 10 is shown in FIG. 1. A single earphone 100 is shown; most systems include a pair of earphones. An ear cup 102 includes an output transducer, or speaker 104, a feedback microphone 106, also referred to as the system microphone, and a feed-forward microphone 108. The speaker 102 divides the ear cup into a front volume 110 and a rear volume 112. The system microphone 106 is typically located in the front volume 110, which is coupled to the ear of the user by a cushion 114. Aspects of the configuration of the front volume in an ANR headphone are described in U.S. Pat. No. 6,597,792, incorporated here by reference. In some examples, the rear volume 112 is coupled to the external environment by one or more ports 116, as described in U.S. Pat. No. 6,831,984, incorporated here by reference. The feed-forward microphone 108 is housed on the outside of the ear cup 102, and may be enclosed as described in U.S. Patent Application 2011/0044465, incorporated here by reference. In some examples, multiple feed-forward microphones are used, and their signals combined or used separately. References herein to the feed-forward microphone include designs with multiple feed-forward microphones.

The microphones and speaker are all coupled to an ANR circuit 118. The ANR circuit may receive additional input from a communications microphone 120 or an audio source 122. In the case of a digital ANR circuit, for example that described in U.S. Pat. No. 8,073,150, incorporated here by reference, software or configuration parameters for the ANR circuit may be obtained from a storage 124. The ANR system is powered by a power supply 126, which may be a battery, part of the audio source 122, or a communications system, for example. In some examples, one or more of the ANR circuit 118, storage 124, power source 126, external microphone 120, and audio source 122 are located inside or attached to the ear cup 102, or divided between the two ear cups when two earphones 100 are provided. In some examples, some components, such as the ANR circuit, are duplicated between the earphones, while others, such as the power supply, are located in only one earphone, as described in U.S. Pat. No. 7,412,070, incorporated here by reference. The external noise to be cancelled by the ANR headphone system is represented as acoustic noise source 128.

When both a feedback ANR circuit and a feed-forward ANR circuit are provided in the same headphone, they are generally tuned to operate over different, but complementary, frequency ranges. When describing the frequency range in which a feedback or feed-forward noise cancellation path is operative, we refer to the range in which the ambient noise is reduced; outside this range, the noise is not altered or may be slightly amplified. Where their operating ranges overlap, the circuits' attenuation may be intentionally reduced to avoid creating a range where the cancellation is greater than everywhere else. That is, the attenuation of an ANR headset may be modified in different frequency ranges to provide a more uniform response than would be achieved by simply maximizing the attenuation within stability or fundamental acoustical limits at all frequencies. Ideally, between the feedback path, the feed-forward path, and the passive attenuation of the headphones, a uniform amount of noise reduction is provided throughout the audible range. We refer to such a system as providing effective cancellation of the ambient sound. To provide the active hear-through features described below, it is preferable that the feedback path have a high-frequency cross-over frequency (where the attenuation drops below 0 dB) above at least 500 Hz. The feed-forward loop will generally operate extending to a higher frequency range than the feedback path.

Figure 2A:
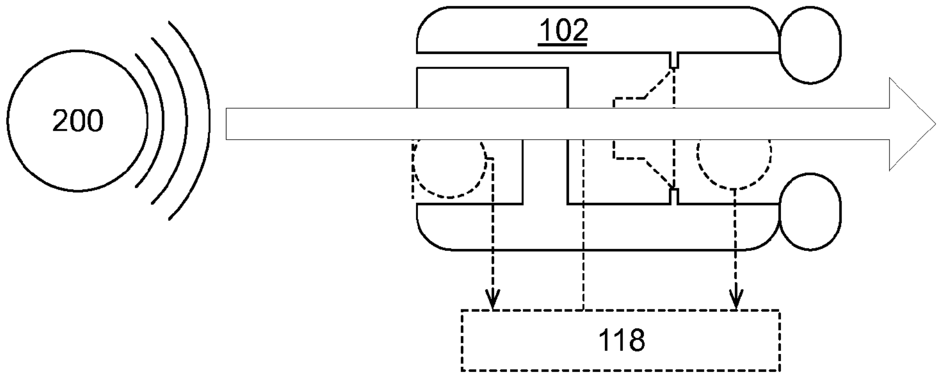
FIG. 2A through 2C show signal paths through an ANR headphone.
Figure 2B:
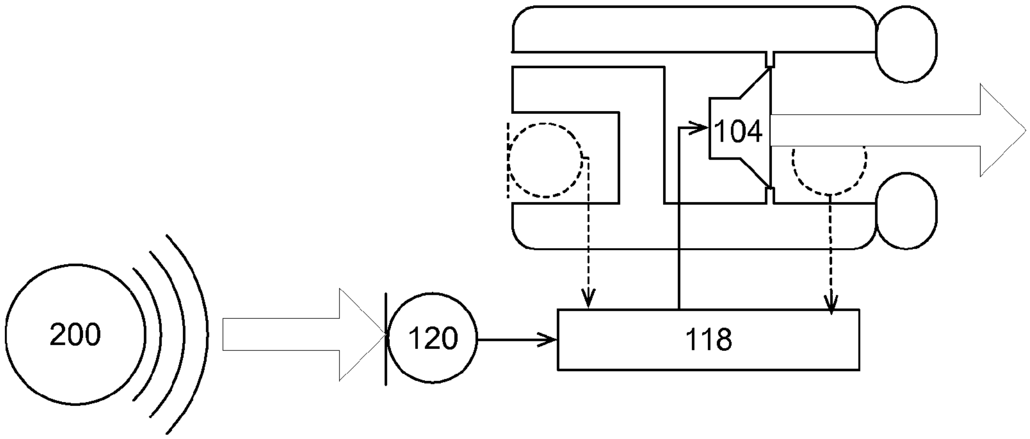
Figure 2C:
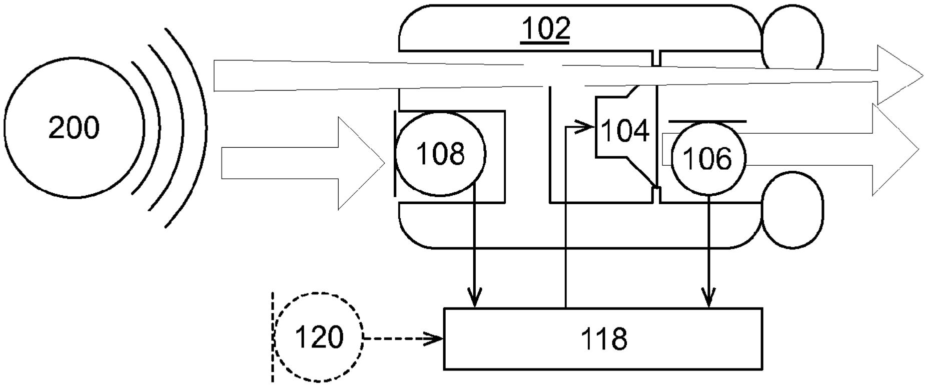

This application concerns improvements to hear-through achieved through sophisticated manipulation of the active noise reduction system. Different hear-through topologies are illustrated in FIGS. 2A through 2C. In the simple version shown in FIG. 2A, the ANR circuit is turned off, allowing ambient sound 200 to pass through or around the ear cup, providing passive monitoring. In the version shown in FIG. 2B, a direct talk-through feature, as discussed above, uses the external microphone 120, coupled to the internal speaker 104 by the ANR circuit or some other circuit, to directly reproduce ambient sounds inside the ear cup. The feedback portion of the ANR system is left unmodified, treating the talk-through microphone signal as an ordinary audio signal to be reproduced, or turned off. The talk-through signal is generally band-limited to the voice band. For this reason, direct talk-through systems tend to sound artificial, as if the user is listening to the environment around him through a telephone. In some examples, the feed-forward microphone serves double duty as the talk-through microphone, with the sound it detects reproduced rather than cancelled.

We define active hear-through to describe a feature that varies the active noise cancellation parameters of a headset so that the user can hear some or all of the ambient sounds in the environment. The goal of active hear-through is to let the user hear the environment as if they were not wearing the headset at all. That is, while direct talk-through as in FIG. 2B tends to sound artificial, and passive monitoring as in FIG. 2A leaves the ambient sounds muddled by the passive attenuation of the headset, active hear-through strives to make the ambient sounds sound completely natural.

Active hear-through (HT) is provided, as shown in FIG. 2C, by using one or more feed-forward microphones 108 (only one shown) to detect the ambient sound, and adjusting the ANR filters for at least the feed-forward noise cancellation loop to allow a controlled amount of the ambient sound 200 to pass through the ear cup 102 with less cancellation than would otherwise be applied, i.e., in normal noise cancelling (NC) operation. The ambient sounds in question may include all ambient sounds, just the voices of others, or the wearer's own voice.

Natural Hear-Through of Ambient Sounds

Providing natural hear-through of ambient sounds, which we refer to as "ambient naturalness," is accomplished through modifications to the active noise cancellation filters. In a system having both feedback and feed-forward noise cancellation circuits, either or both cancellation circuits can be modified. As explained in U.S. Pat. No. 8,155,334, incorporated herein, a feed-forward filter implemented in a digital signal processor can be modified to provide talk-through by not completely cancelling all or a subset of the ambient noise. In the example of that application, the feed-forward filters are modified to attenuate sounds within the human speech band less than they attenuate sounds outside that band. That application also suggests providing parallel analog filters, one for full attenuation and one with reduced attenuation in the speech band, as an alternative to digital filters.

Figure 3:
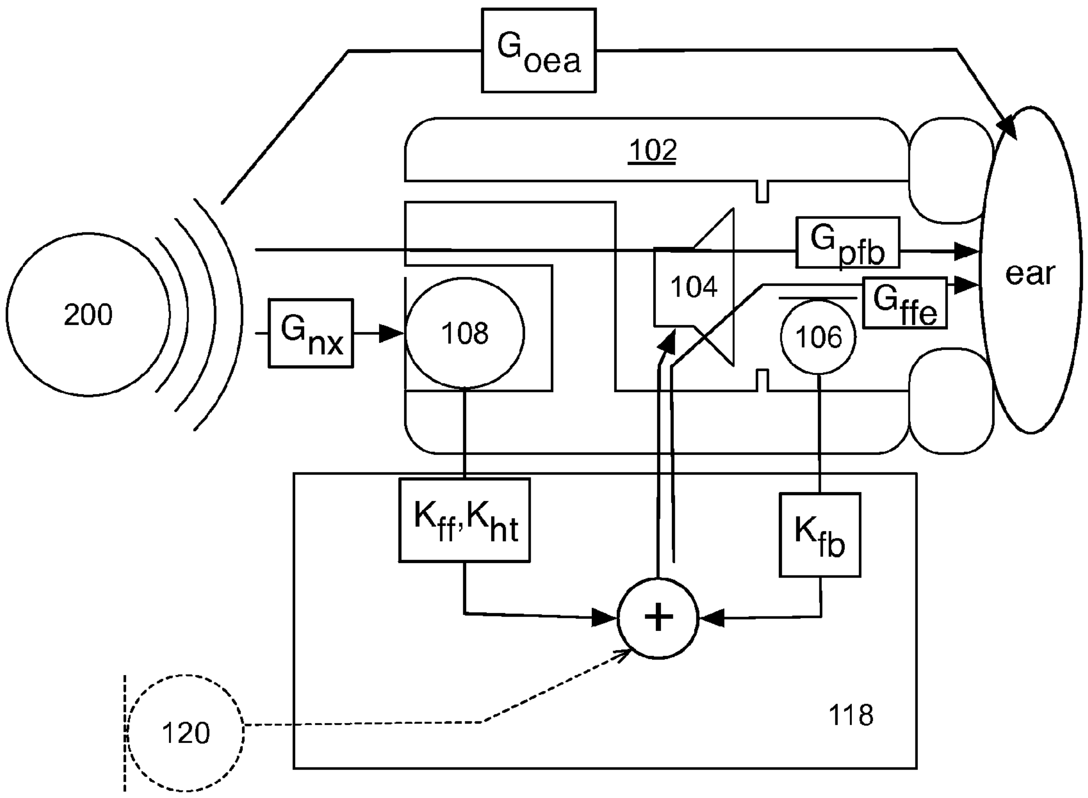
FIGS. 3, 6, and 8 show block diagrams of an ANR headphone with active hear-through capabilities.

To make the sounds that are allowed to pass sound more natural, compensating for the changes in the sound resulting from the passive attenuation, and providing natural hear-through over the full range of audio frequencies, the feed-forward filters can be modified in more sophisticated ways. FIG. 3 shows a block diagram of an ANR circuit used in an example like FIG. 2C and the related components. We refer to the effect of various components on sounds moving between the various points in the system as the response or transfer function. Several responses of interest are defined as follows:

a) $G_{oea}$: Response from noise to ear, without the headphones
b) $G_{pfb}$: Response from noise to ear, through the headphones and with feedback ANR active
c) $G_{nx}$: Response from noise to external (feed-forward) microphone
d) $G_{ffe}$: Response of the output of the feedback filter and any signals summed with it, through the driver 104, to the ear, with the feedback ANR active The various electronic signal pathways of the ANR circuit apply the following filters, which we may refer to as gains of the pathways:

a) $K_{fb}$: Gain of the feedback compensation filter
b) $K_{ff}$: Gain of the feed-forward compensation filter
c) $K_{ht}$: Gain of the active hear-through filter (in FIG. 3, $K_{ff}$ and $K_{ht}$ are alternately applied to the same pathway)

We define the target hear-through insertion gain, i.e., how the total system should filter the ambient sound, as $T_{htig}$. If $T_{htig}=1$ (0 dB), then the user should hear the world around them the same as they would if not wearing headphones. In practice, a target value other than 0 dB is often desired. For example, cancellation at low frequencies, such as below 100 Hz, is still useful during an active hear-through mode, as such sounds tend to be unpleasant and to not contain useful information. However, a $T_{htig}$ pass-band that extends to cover at least the range of 300 Hz to 3 kHz is necessary for the voices of those around the user to be clearly understandable. Preferably the pass-band extends from 140 Hz to 5 kHz to approach a sense of naturalness. The pass-band may be shaped to improve perception of the naturalness in an active hear-through mode, For example, a gentle high-frequency roll-off may compensate for the distortion of spatial hearing caused by the presence of the headphones. Ultimately, the filter should be designed to provide a total system response that is smooth and piecewise-linear. By "smooth and piecewise-linear," we are referring to the general shape of a plot of the system response on a dB/log-frequency scale.

Combining these factors, the total response at the ear to ambient noise when wearing the headphones is $G_{pfb}+G_{nx}*K_{ht}*G_{ffe}$. The desired response is $G_{oea}*T_{htig}$. That is, the combination of the passive and feedback response Go, with the actual hear-through response $G_{nx}*K_{ht}*G_{ffe}$ should sound like the target hear-through insertion gain $T_{htig}$ applied to the open-ear response $G_{oea}$. The system is tuned to deliver the desired response by measuring the various actual responses (the $G_{xx}$ terms) and defining the filter $K_{ht}$, within the limits of realizability, to bring the actual system response as close as possible to the target, based on the equation:

$$T_{htig} = \frac{G_{pfb}}{G_{oea}} + \frac{K_{ht} * G_{nx} * G_{ffe}}{G_{oea}} \quad (1)$$

Solving equation (1) for $K_{ht}$ leads to:

$$K_{ht} = \frac{G_{oea}}{G_{nx} G_{ffe}} \left( T_{htig} - \frac{G_{pfb}}{G_{oea}} \right) \quad (2)$$

To best achieve the desired $T_{htig}$, the filter $K_{ht}$ implemented in the feed-forward signal path may be non-minimum phase, i.e., it may have zeros in the right half plane. This can, for example, allow active hear-through to pass human speech while canceling the ambient rumble present in many buildings due to heating and cooling systems. Such a combination is provided by designing $K_{ht}$ so that $T_{htig}$ approaches 0 dB only in the active hear-through passband. Outside the active hear-through passband, $K_{ht}$ is designed such that $T_{htig}$ approaches, and ideally equals, the insertion gain (which is actually an insertion loss) achieved by a feed-forward filter that results in significant attenuation (i.e., the usual $K_{ff}$). The sign of the feed-forward filter required for effective attenuation ($K_{ff}$) and active hear-through ($K_{ht}$) are, in general, opposite in the hear-through passband. Designing a $K_{ht}$ that rolls off at the low-frequency edge of the passband and transitions to an effective $K_{ff}$ response can be achieved by including at least one right-half-plane zero in the vicinity of that transition.

In total, replacing the feed-forward filter $K_{ff}$ with the active hear-through filter $K_{ht}$, while maintaining the feedback loop $K_{fb}$, enables the ANR system to combine with the passive acoustic path through the headphone to create a natural experience at the ear that sounds the same as if the headphone were not present. To allow $K_{ht}$ to deliver the intended sound of the outside world, the feedback loop in combination with the passive acoustic path through the headphone should provide at least 8 dB of attenuation at all frequencies of interest. That is, the noise level heard at the ear when the feedback loop is active, but the feed-forward path is not, should be less than the noise level at the ear when the headphones aren't worn at all by at least 8 dB (note that "less than by 8 dB" refers to the ratio of levels, not a number of decibels on some external scale). When $G_{pfb}$ is less than or equal to −8 dB, the effect it has on the actual hear-through insertion gain is less than 3 dB error when the desired $T_{htig}$=0 dB. The attenuation may be much higher, if the feedback loop is capable of more gain, or the passive attenuation is greater. To achieve this naturalness in some cases, it may also be desirable to reduce the gain $K_{fb}$ of the feedback loop from its maximum capability, as discussed below.

The difference in overall noise reduction at the ear between the normal ANR mode and the active hear-through model should be at least 12 dBA. This provides enough of a change in ambient noise level that switching from active hear-through mode with quiet background music to noise reduction results in a dramatic change. This is because of the rapid decrease in the perceived loudness of the ambient noise in the presence of the music masker when switching modes. The music, which is quietly in the background in hear-through mode, can make the noise virtually inaudible in noise reduction mode as long as there is at least 12 dBA of noise reduction change between the hear-through and noise reduction modes.

In some examples, a digital signal processor like that described in U.S. Pat. No. 8,184,822, incorporated here by reference, advantageously sums the output of the feedback loop with the path through the fed-forward microphone, avoiding the combing (deep nulls in the combined signal) that might result if $K_{ht}$ has a latency typical of an audio-quality ADC/DAC combination, typically several hundred microseconds. Preferably, the system is implemented using a DSP having a latency of less than 250 μs so that the first potential null from combing (which will be at 2 kHz with 250 μs latency) is at least one octave above the typical minimum insertion loss frequency in $G_{pfb}$, which is typically around 1 khz. The configurable processor described in the cited patent also allows easy substitution of the active hear-through filter $K_{ht}$ for the feed-forward filter $K_{ff}$.

Once ambient naturalness is achieved, additional features may be provided by selecting between more than one feed-forward filter $K_{ht}$, providing different total response characteristics. For example, one filter may be preferable for providing hear-through in an aircraft, where loud, low-frequency sounds tend to mask conversation, so some cancellation in that frequency should be maintained, while voice-band signals should be passed as naturally as possible. Another filter may be preferable in generally quieter environments, where the user wants or needs to hear the environmental sounds accurately, such as to provide situational awareness when walking down the street. Selecting between active hear-through modes may be done using a user interface, such as buttons, switches, or an application on a smart phone paired to the headset. In some examples, the user interface for selecting a hear-through mode is a volume control, with different hear-through filters being selected based on the volume setting chosen by the user.

The hear-through filter selection may also be automatic, in response to ambient noise spectrum or level. For example, if the ambient noise is generally quiet or generally broad-spectrum, a broad-spectrum hear-through filter may be selected, but if the ambient noise has a high signal content at a particular frequency range, such as that of aircraft engines or the roar of a subway, that range may be cancelled more than providing ambient naturalness would call for. The filter may also be selected to provide broad-spectrum hear-through but at reduced volume levels. For example, setting $T_{htig}$=0.5 will provide 6 dB of insertion loss over a broad frequency range. The measurement of ambient sounds used to automatically select the hear-through filters may be a time-average measurement of the spectrum or level, which may be updated periodically or continuously. Alternatively, the measurement may be made instantaneously at the time the user activates the hear-through mode, or a time average of a sample time immediately prior to or immediately after the user makes the selection may be used.

One example use for an automatically-selected set of active hear-through filters is industrial hearing protection. A headphone having feedback and feed-forward active noise reduction, plus passive attenuation, that delivers 20 dB attenuation could be used to protect hearing, to accepted standards, in noise levels as high as 105 dBA (i.e., it reduces the noise 20 dB from 105 dBA to 85 dBA), which covers the vast majority of industrial noise environments. However, in an industrial environment where the noise level changes over time or with location, one doesn't want the full 20 dB of attenuation when it is comparatively quiet (e.g., less than 70 dBA) since it hinders communication between workers. A multi-mode active hear-through headphone can function as a dynamic noise reduction hearing protector. Such a device would monitor the ambient level at the feed-forward microphones and, if the level is below 70 dBA, apply a filter $K_{ht}$ to the feed-forward path that creates a $T_{htig}$=0 dB. As the noise levels increases above 70 dBA, the headphone detects this and steps through several sets of $K_{ht}$ filter parameters (such as from a lookup table) to gradually reduce the insertion gain. Preferably, the headphone will have many possible sets of filters to apply and the detection of ambient level be done with a long time constant. The audible effect would be to compress a slow increase from 70 to 105 dBA in actual noise level around the user to a perceived increase from 70 to only 85 dBA, while continuing to pass the short-term dynamics of speech and the noise.

The figures and description above consider a single ear cup. In general, active noise reducing headphones have two ear cups. In some examples, the same hear-through filters are applied for both ear cups, but in other examples, different filters may be applied, or the hear-through filter $K_{ht}$ may be applied to only one ear cup while the feed-forward cancellation filter $K_{ff}$ is maintained in the other ear cup. This may be advantageous in several examples. If the headphone is a pilot's headset used for communication with other vehicles or a control center, turning on hear-through in only one ear cup may allow the pilot to speak with a crew member not wearing a headset while maintaining awareness of communication signals or warnings by keeping noise cancellation active in the other ear cup.

The active hear-through performance may be enhanced if the feed-forward microphone signals of each ear cup are shared with the other ear cup, and inserted into each opposite ear cup's signal path using another set of filters $K_{xo}$. This can provide directionality to the hear-through signal, so the wearer is better able to determine the source of sounds in their environment. Such improvements may also increase the perceived relative level of the voice of a person on-axis in front of the wearer, relative to diffuse ambient noise. A system capable of providing the cross-over feed-forward signals is described in U.S. Patent Application publication 2010/0272280, incorporated here by reference.

Figure 7:
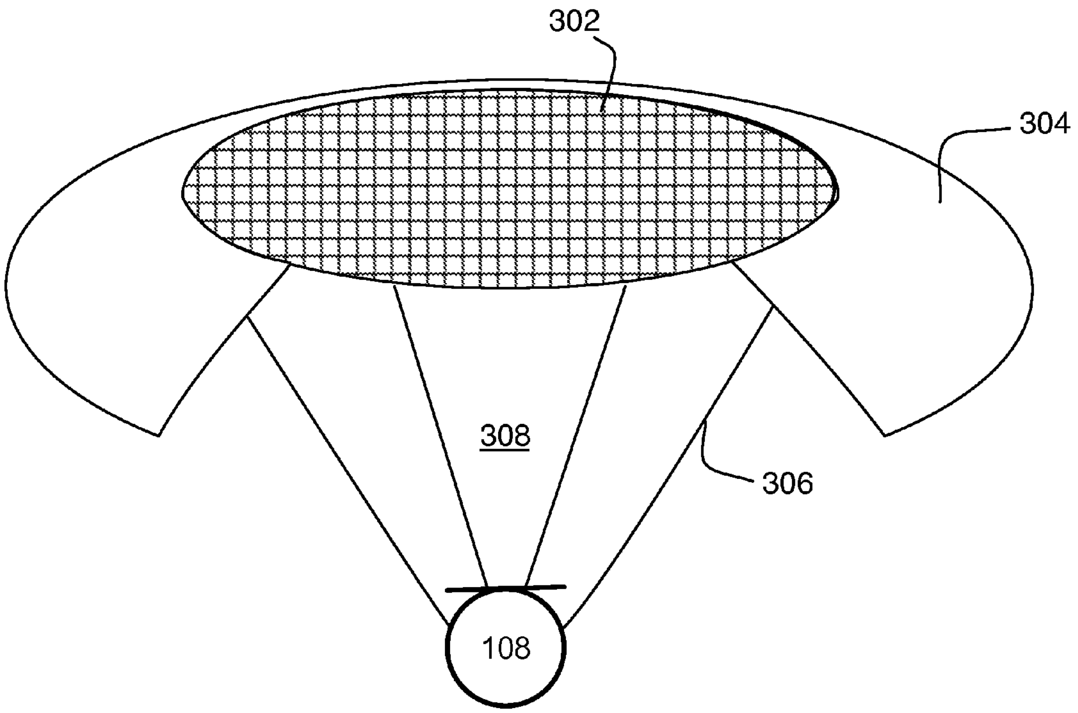
FIG. 7 shows a schematic diagram of a microphone housing.

In addition to using active noise cancellation techniques to provide both ANR and hear-through, an active hear-through system may also include a single-channel noise reduction filter in the feed-forward signal path during the hear-through mode. Such a filter may clean up the hear-through signal, for example improving the intelligibility of speech. Such in-channel noise reduction filters are well-known for use in communications headsets. For best performance, such a filter should be implemented within the latency constraints described above When the feed-forward microphone is used to provide active hear-through of ambient sounds, it may be beneficial to protect the microphone against wind noise, that is, noise caused by air moving quickly past the microphone. Headsets used indoors, such as on aircraft, generally do not need wind noise protection, but headsets that may be used outdoors may be susceptible. As shown abstractly in FIG. 7, an effective way to protect the feed-forward microphone 108 from wind noise is to provide a screen 302 over the microphone and to provide some distance between the screen and the microphone. In particular, the distance between the screen and the microphone should be at least 1.5 mm, while the aperture in the ear cup outer shell 304, covered by the screen 302, should be as large as possible. Given the practical considerations of fitting such components in an in-ear headphone, the screen area should be at least 10 $mm^2$, and preferably 20 $mm^2$ or larger. The total volume enclosed by the screen and sidewalls 306 of the cavity 308 around the microphone 108 is not as important, so the space around the microphone may be cone-shaped, with the microphone at the apex and the angle of the cone selected to provide as much screen area as other packaging constraints allow. The screen should have some appreciable acoustic resistance, but not so great as to decrease the sensitivity of the microphone to uselessly low levels. Acoustically resistive cloth having a specific acoustic resistance between 20 and 260 Rayls (MKS) has been found to be effective. Such protections may also be of value for general noise reduction as well, if the headphones are to be used in a windy environment, by preventing wind noise from saturating the feed-forward cancellation path.

Natural Hear-Through of the User's Voice

When a person hears their own voice as sounding natural, we refer to this as "self naturalness." As just described, ambient naturalness is accomplished through modifications of the feed-forward filter. Self naturalness is provided by modifying the feed-forward filters and the feedback system, but the changes are not necessarily the same as those used when ambient naturalness alone is desired. In general, simultaneously achieving ambient naturalness and self naturalness in active hear-through requires altering both the feed-forward and feedback filters.

Figure 4:
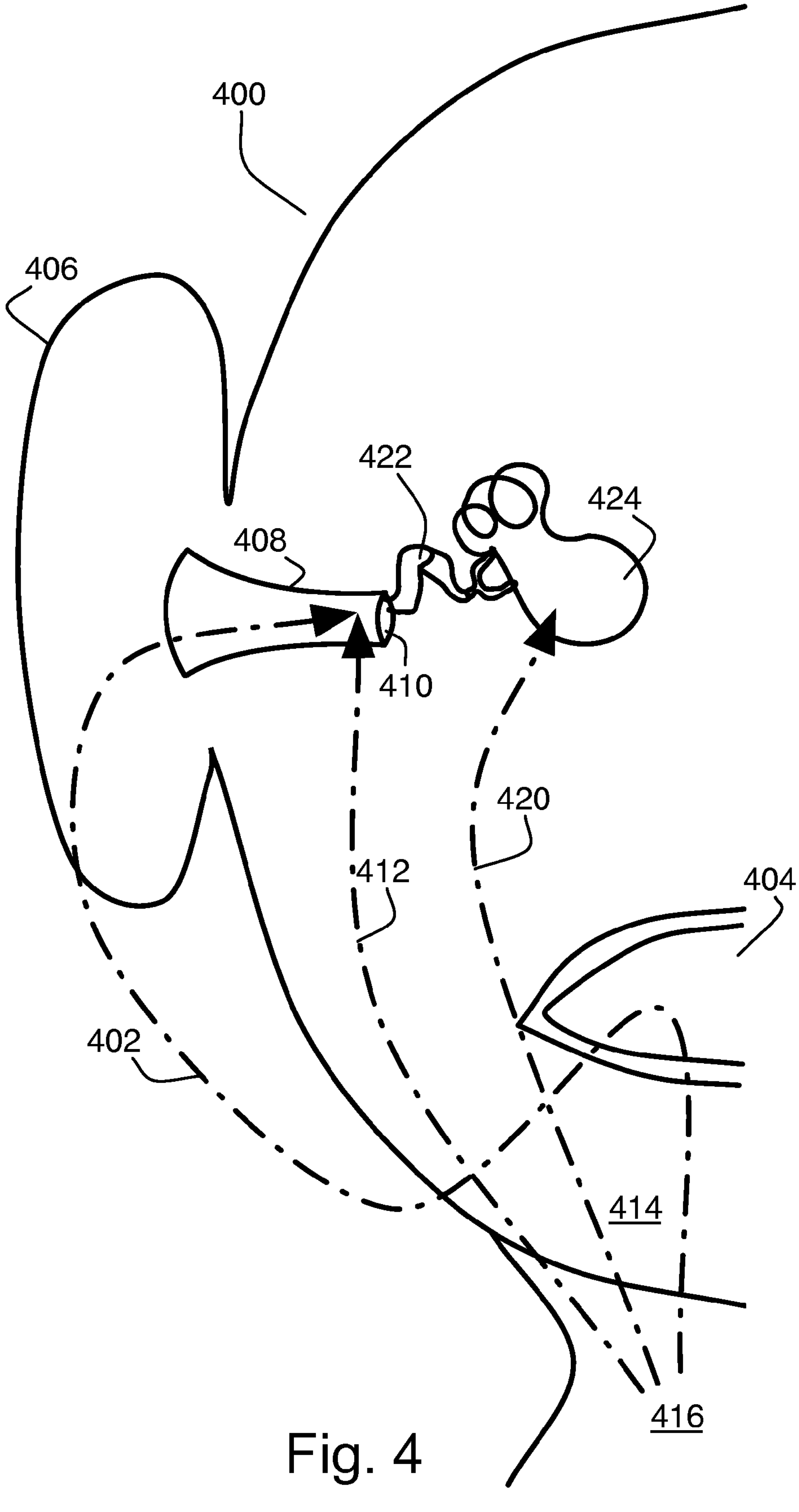
FIG. 4 shows a schematic diagram acoustic signal paths from the larynx to the inner ear of a human.

As shown in FIG. 4, a person generally hears his own voice through three acoustic paths. The first path 402 is through the air around the head 400 from the mouth 404 to the ear 406 and into the ear canal 408 to reach the ear drum 410. In the second path 412, sound energy travels through the soft tissues 414 of the neck and head, from the larynx 416 to the ear canal 408. The sound then enters the air volume inside the ear canal through vibrations of the ear canal walls, joining the first path to reach the ear drum 410, but also escaping out through the ear canal opening into the air outside the head. Finally, in the third path 420, sound also travels through the soft tissues 414 from the larynx 416, as well as through the Eustachian tubes connecting the throat to the middle ear 422, and it goes directly to the middle ear 422 and inner ear 424, bypassing the ear canal, to join with sound coming through the ear drum from the first two paths. In addition to providing different levels of signal, the three paths contribute different frequency components of what the user hears as his own voice. The second path 412 through soft tissues to the ear canal is the dominant body-conducted path at frequencies below 1.5 kHz and, at the lowest frequencies of the human voice, can be as significant as the air-conducted path. Above 1.5 kHz, the third path 420 directly to the middle and inner ear is dominant.

When wearing headphones, the first path 402 is blocked to some degree, so the user can't hear that portion of his own voice, changing the mix of the signals reaching the inner ear. In addition to the contribution from the second path providing a greater share of the total sound energy reaching the inner ear due to the loss of the first path, the second path itself becomes more efficient when the ear is blocked. When the ear is open, the sound entering the ear canal through the second path can exit the ear canal through the opening of the ear canal. Blocking the ear canal opening improves the efficiency of coupling of ear canal wall vibration into the air of the ear canal, which increases the amplitude of pressure variations in the ear canal, and in turn increases the pressure on the ear drum. This is commonly called the occlusion effect, and it can amplify sounds at the fundamental frequencies of a male voice by as much as 20-25 dB. As a result of these changes, the user perceives their voice to have over-emphasized lower frequencies and under-emphasized higher frequencies. In addition to making the voice sound lower, the removal of the higher frequency sounds from human voice will also make the voice less intelligible. This change in the user's perception of their own voice can be addressed by modifying the feed-forward filters to admit the air-conducted portion of the user's voice, and modifying the feedback filters to counteract the occlusion effect. The changes to the feed-forward filters for ambient naturalness, discussed above, are generally sufficient to provide self naturalness as well, if the occlusion effect can be reduced. Reducing the occlusion effect may have benefits beyond self-naturalness, and is discussed in more detail below.

Reduction of the Occlusion Effect

The occlusion effect is particularly strong when the headphone is just capped, i.e., by headphones that block the entrance to the ear canal directly, but do not protrude far into the ear canal. Larger volume ear cups provide more room for sounds to escape the ear canal and dissipate, and deep-canal earphones block some of the sound from passing from the soft tissues into the ear canal in the first place. If the headphones or earplugs extend far enough into the ear canal, past the muscle and cartilage to where the skin is very thin over the bone of the skull, the occlusion effect goes away, as little sound pressure enters the enclosed volume through the bone, but extending a headphone that far into the ear canal is difficult, dangerous, and can be painful. For any type of headphone, reducing whatever amount of occlusion effect is produced can be beneficial for providing self naturalness in an active hear-through feature and for removing non-voice elements of the occlusion effect.

Figure 6:
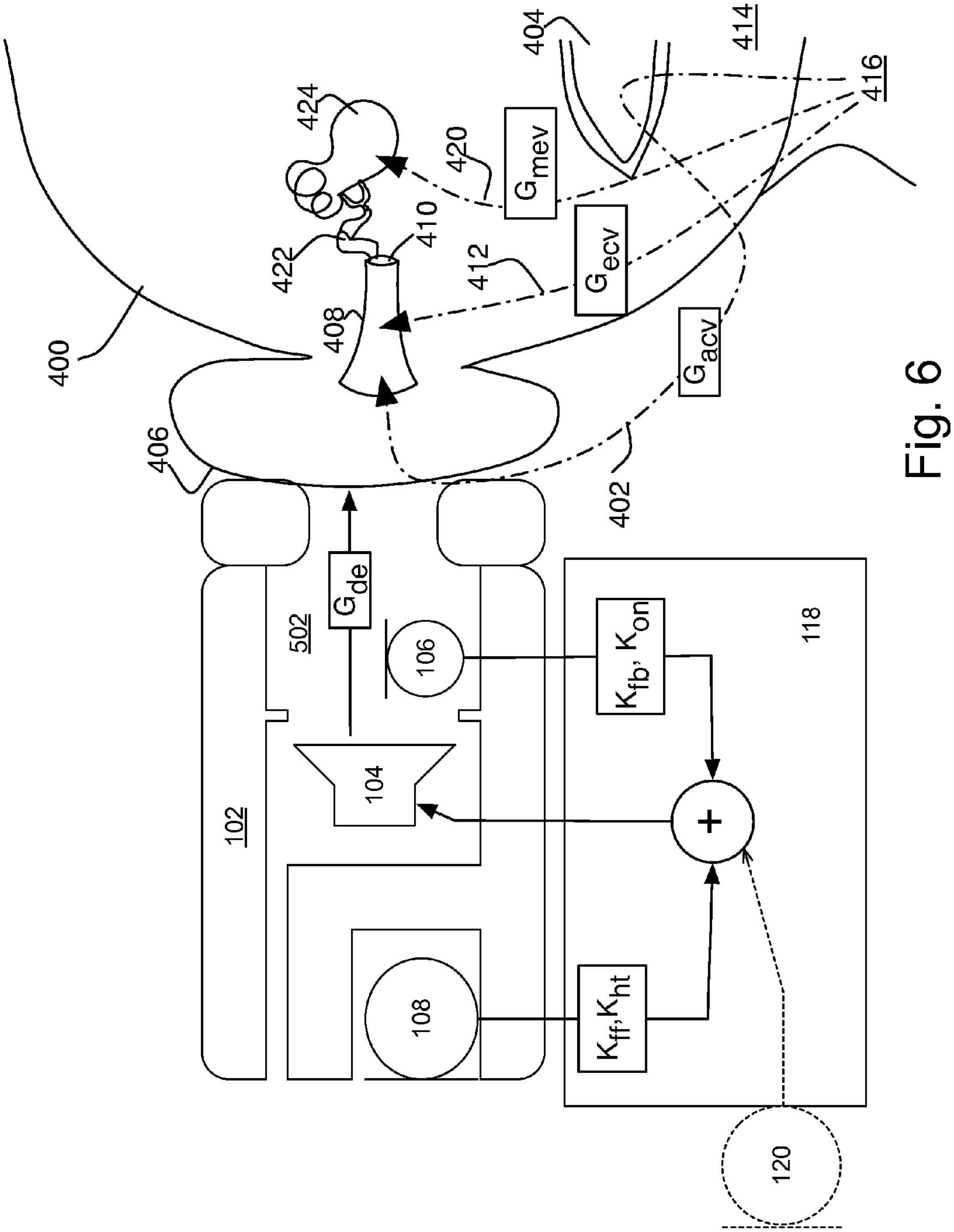

The experience of wearing headphones is improved by eliminating the occlusion effect, so that the user hears their own voice naturally when active hear-through is provided. FIG. 6 shows a schematic diagram of the head-headphone system and various signal paths through it. The external noise source 200 and related signal paths from FIG. 3 are not shown but may be present in combination with the user's voice. The feedback system microphone 106 and compensation filter $K_{fb}$ create a feedback loop that detects and cancels sound pressure inside the volume 502 bounded by the headphones 102, the ear canal 408, and the eardrum 410. This is the same volume where the amplified sound pressure at the end of path 412 causing the occlusion effect is present. As a result of the feedback loop reducing the amplitude of oscillations in this pressure (i.e., sound), the occlusion effect is reduced or eliminated by the ordinary operation of the feedback system.

Reducing or even eliminating the negative consequences of the occlusion effect may be accomplished without perfect cancellation of the sound pressure. Some feedback-based noise cancelling headphones are capable of providing more cancellation than is needed to mitigate the occlusion effect. When the goal is only to remove the occlusion effect, the feedback filters or gain are adjusted to provide just enough cancellation to do that, without further cancelling ambient sounds. We represent this as applying filter $K_{on}$ in place of the full feedback filter $K_{fb}$.

Figure 5A:
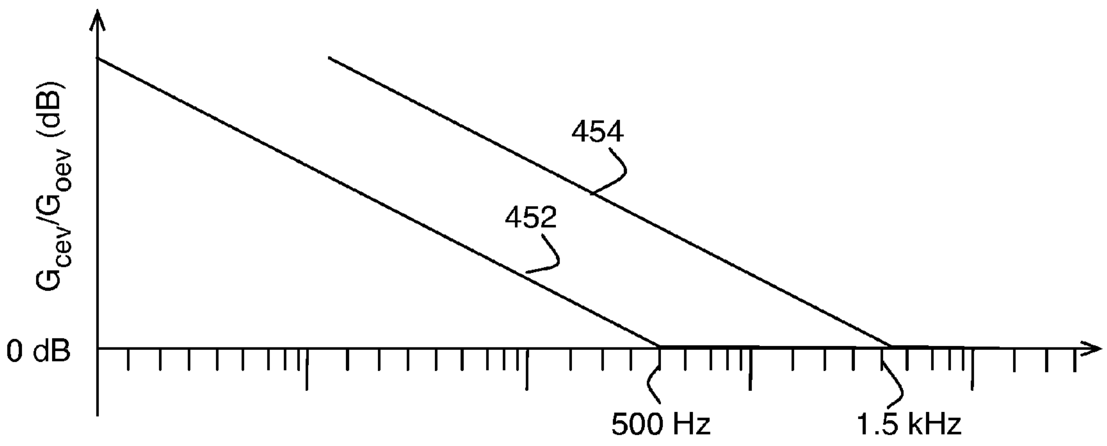
FIG. 5A shows a graph of occlusion effect magnitude.
Figure 5B:
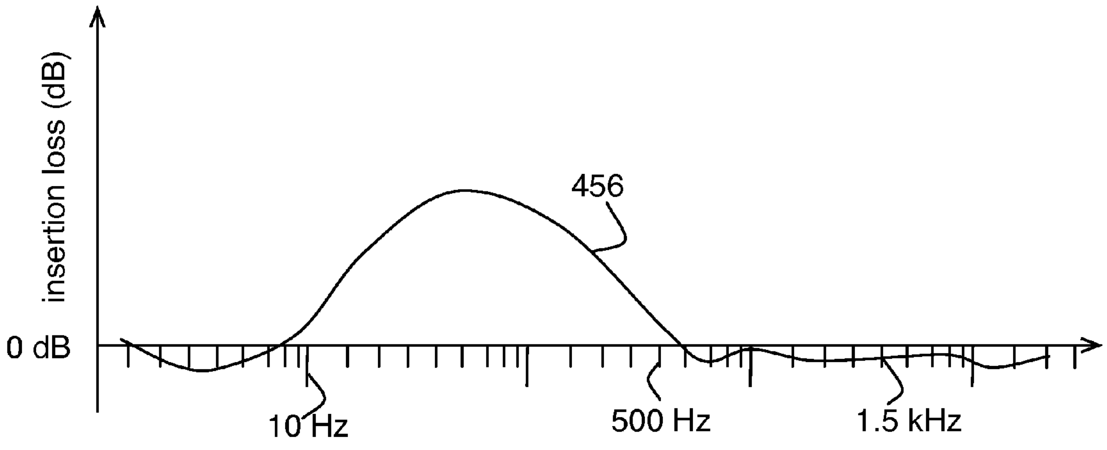
FIG. 5B shows a graph of insertion loss for a noise reduction circuit.

As shown in FIG. 5A, the occlusion effect is most pronounced at low frequencies, and decreases as frequency increases, becoming imperceptible (0 dB) somewhere in the mid frequency range, between around 500 Hz and 1500 Hz, depending on the particular design of the headphone. The two examples in FIG. 5A are an around-ear headphone, curve 452, for which the occlusion effect ends at 500 Hz, and an in-ear headphone, curve 454, for which the occlusion effect extends to 1500 Hz. Feedback ANR systems are generally effective (i.e., they can reduce noise) in low to mid frequency ranges, losing their effectiveness somewhere in the same range where the occlusion effect ends, as shown in FIG. 5B. In the example of FIG. 5B, the insertion loss (i.e., decrease in sound from outside to inside the ear cup) curve 456 due to the ANR circuit crosses above 0 dB at around 10 Hz and crosses back below 0 dB at around 500 Hz. If the feedback ANR system in a given headphone is effective to frequencies above where the occlusion effect ends in that headphone, such as curve 452 in FIG. 3B, the feedback filter can be reduced in magnitude and still remove the occlusion effect entirely. On the other hand, if the feedback ANR system stops providing effective noise reduction at a frequency below where the occlusion effect ends for that headphone, such as curve 454 in FIG. 5A, then the full magnitude of the feedback filter will be needed, and some occlusion effect will remain.

As with the feed-forward system, filter parameters for the feedback system to achieve self naturalness by eliminating the occlusion effect as much as possible can be found from the responses of the various signal paths in the head-headphone system shown in FIG. 6. In addition to those that are the same as in FIG. 3, the following responses are considered:

a) $G_{ac}$: The response of air-conducted path 402 from the mouth to the ear (unobstructed by the headphone, as in FIG. 4)

b) $G_{bcc}$: The response of the body-conducted path 412 to the ear canal (when the ear canal is not blocked by the headphone)

c) $G_{bcm}$: The response of the body-conducted path 420 to the middle and inner ear The body-conducted responses $G_{bcc}$ and $G_{bcm}$ are significant at different frequency ranges, generally below and above 1.5 kHz, respectively. These three paths combine to form the net open-ear response of the user's voice at the ear canal, without the headphones, $G_{oev}=G_{ac}+G_{bcc}+G_{bcm}$. In contrast, the net closed-ear voice response when the headphones are present is defined as $G_{cev}$.

The net responses $G_{oev}$ or $G_{cev}$ can't be measured directly with any repeatability or precision, but their ratio $G_{cev}/G_{oev}$ can be measured by suspending a miniature microphone in the ear canal (without blocking the ear canal) and finding the ratio of the spectrum measured when the subject speaks while wearing the headphone to the spectrum measured when the subject speaks without wearing the headphone. Performing the measurement on both ears, with one obstructed by the headphone and the other open, guards against errors resulting from the variability of human speech between measurements. Such measurements are the source of the occlusion effect curves in FIG. 5A.

To find the value of $K_{on}$ to use to just cancel the occlusion effect, we consider the effect of the headphones and ANR system on the responses as they combine to form $G_{cev}$. A reasonable approximation is that $G_{ac}$ is affected the same way as air-conducted ambient noise, so its contribution to $G_{cev}$ is $G_{ac}*(G_{pfb}+G_{nx}*K_{ht}*G_{ffe})$. The headphones have a negligible effect on the third path 420 directly to the middle and inner ear, so $G_{bcm}$ remains unchanged. As for the second path 412, the body-conducted sound entering the ear canal is indistinguishable from ambient noise that gets past the ear cup, so the feedback ANR system cancels it with the feedback loop occlusion filter $K_{on}$, providing a response of $G_{bcc}/(1-L_{fb})$, where loop gain $L_{fb}$ is the product of the feedback filter $K_{on}$ and the driver-to-system-microphone response $G_{ds}$. In total, then, $$G_{cev} = G_{ac} * (G_{pfb} + G_{nx} * K_{ht} * G_{ffe}) + \frac{G_{bcc}}{(1 - L_{fb})} + G_{bcm} \quad (3)$$

and $$\frac{G_{cev}}{G_{oev}} = \frac{G_{ac} * (G_{pfb} + G_{nx} * K_{ht} * G_{ffe}) + \frac{G_{bcc}}{(1 - L_{fb})} + G_{bcm}}{G_{ac} + G_{bcc} + G_{bcm}} \quad (4)$$

For self-naturalness, one wants Gcev/Goev=1 (0 dB). Combined with the earlier equation (1) for self-naturalness, this allows balancing these two aspects of the hear-thru experience. Human perception of ambient sound is largely insensitive to phase (assuming the phase does not change very rapidly) so the phase response resulting from the value of $K_{ht}$ chosen to approximate $T_{htig}$ is not significant. What matters in solving equation (1) for $K_{ht}$ is matching the magnitude $|T_{htig}|$. The phase of $G_{pfb}+G_{nx}*K_{ht}*G_{ffe}$ will, however, affect how the covered-ear $G_{ac}$ path (affected by $K_{ht}$) sums with the covered-ear $G_{bcc}$ path (affected by $K_{on}$). The design process breaks into the following steps:

a) Measure the occlusion effect (the low frequency boost in $G_{cev}/G_{oev}$) by measuring $G_{cev}$ with all ANR turned off.
b) Design the ANR feedback loop to counter-balance the measured occlusion effect. If the measurements show 10 dB of occlusion effect boost at 400 Hz then one would, to first approximation, want 10 dB of feedback loop desensitivity (1−Lfb) at that frequency. For headphones that don't have enough feedback ANR gain to fully cancel the occlusion effect, $K_{on}$ will simply be equal to the $K_{fb}$ of the optimized feedback loop. For headphones that do have sufficient headroom in the feedback loop, $K_{on}$ will be some value less than $K_{fb}$.
c) Design $K_{ht}$ for ambient naturalness as discussed above.
d) Apply the $K_{ht}$ filter to the feed-forward loop and $K_{on}$ to the feedback loop and measure $G_{cev}/G_{oev}$ again.
e) Adjust the phase of $K_{ht}$ without altering the magnitude by adding all-pass filter stages or moving zeros into the right half plane (or outside the unit circle in digital systems) to minimize any deviation in $G_{cev}/G_{oev}$ from 1 (transparency).
f) It may also be beneficial to adjust $K_{on}$ in this process. Updated values of $K_{on}$ and $K_{ht}$ are iterated to find the best balance of desired ambient response and own-voice response.

Reducing the occlusion effect and allowing the wearer to hear his own voice naturally has a further benefit of encouraging the user to speak at a normal level when talking to someone else. When people are listening to music or other sounds on headphones, they tend to speak too loudly, as they speak loudly enough to hear themselves over the other sound they hear, even though no-one else can hear that sound. Conversely, when people are wearing noise-cancelling headphones but not listening to music, they tend to speak too softly to be understood by others in a noisy environment, apparently because in this case they easily hear their own voice over the quiet residual ambient noise they hear. The way people adjust their own speaking level in response to how they hear their own voice in relation to other environmental sounds is called the Lombard Reflex. Allowing the user to accurately hear the level of his own voice via active hear-through allows him to correctly control that level. In the case of music playing in the headphones causing the user to speak too loudly, muting the music when switching into the hear-through mode could also help the user to correctly hear his own voice and control its level.

Retaining Entertainment Audio During Active Hear-Through

Figure 8:
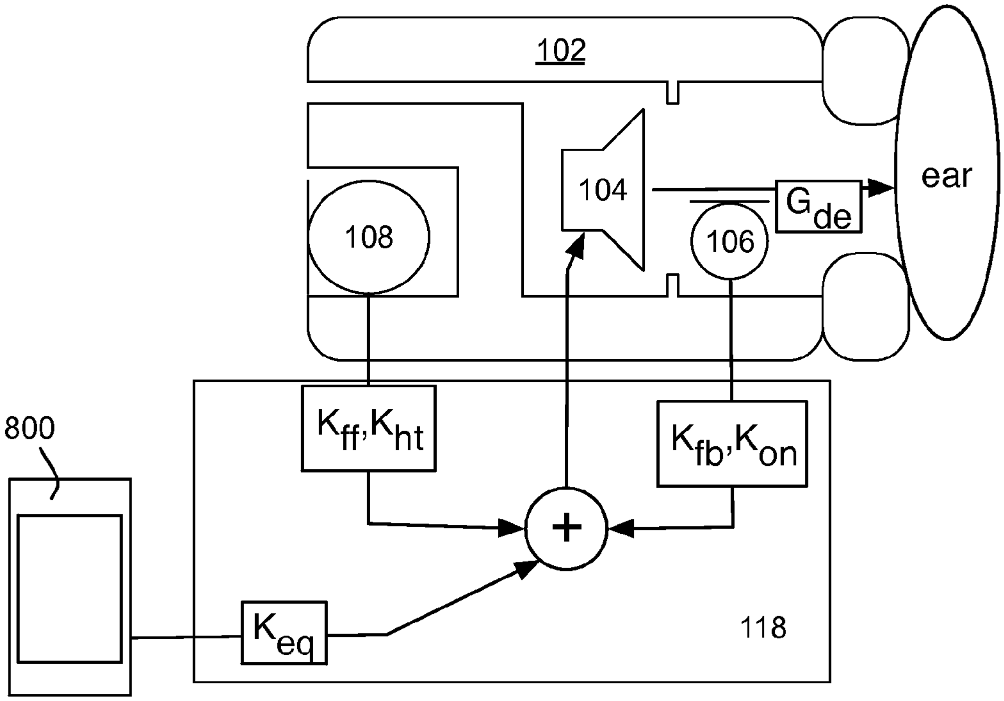

Headphones that provide direct talk-through or passive monitoring by muting the ANR circuit and either reproducing the external sounds or allowing them to passively move through the headphones also mute any input audio, such as music, that they may be reproducing. In the system described above, active noise reduction and active hear-through can be provided independently of reproduction of entertainment audio. FIG. 8 shows a block diagram like that in FIGS. 3 and 5, modified to also show the audio input signal path. The external noise and related acoustic signals are not shown for the sake of clarity. In the example of FIG. 8, the audio input source 800 is connected to the signal processor, filtered by a equalizing audio filter $K_{eq}$, and combined with the feedback and feed-forward signal paths to be delivered to the output transducer 104. The connection between the source 800 and the signal processor may be a wired connection, through a connector on the ear cup or elsewhere, or it may be a wireless connection, using any available wireless interface, such as Bluetooth®, Wi-Fi, or proprietary RF or IR communications.

Providing a separate path for the input audio allows headphones to be configured to adjust the active ANR to provide active hear-through, but at the same time keep playing the entertainment audio. The input audio may be played at some reduced volume, or kept at full volume. This allows a user to interact with others, such as a flight attendant, without missing whatever they are listening to, such as the dialog of a movie. Additionally, it allows users to listen to music without being isolated from their environment, if that is their desire. This allows the user to wear the headphones for background listening while maintaining situational awareness and remaining connected with their environment. Situational awareness is valuable, for example, in urban settings where someone walking down the street wants to be aware of people and traffic around them but may want to listen to music to enhance their mood or to podcasts or radio for information, for example. They may even wear the headphone to send a "do not disturb" social signal while actually wanting to be aware of what's going on around them. Even if situational awareness is not of value, for example, a user listening to music at home without other disturbances, some users may prefer to be aware of the environment, and to not have the isolation that even passive headphones typically provide. Keeping active hear-through enabled while listening to music provides this experience.

The specifics of the feed-forward and input audio signal path filters will affect how active hear-through interacts with reproduction of input audio signals to produce a total system response. In some examples, the system is tuned so that the total audio response is the same in both noise-canceling mode and active hear-through mode. That is, the sound reproduced from the input audio signal sounds the same in both modes. If $K_{on} \neq K_{fb}$, then $K_{eq}$ must differ in the two modes by the change in desensitivity from $1-G_{ds}K_{fb}$ to $1-G_{ds}K_{on}$. In some examples, the frequency response is kept the same, but the gains applied to the input audio and feed-forward paths are modified. In one example, the gain in $K_{eq}$ is reduced during active hear-through mode so that the output level of the input audio is reduced. This can have the effect of keeping the total output level constant between active noise cancellation mode, where the input audio is the only thing heard, and the hear-through mode, where the input audio is combined with the ambient noise.

In another example, the gain in $K_{eq}$ is increased during the active hear-through mode, so that the output level of the input audio is increased. Raising the volume of the input audio signal decreases the extent to which the ambient noise that is inserted during active hear-through masks the input audio signal. This can have the effect of preserving the intelligibility of the input audio signal, by keeping it louder than the background noise, which of course increases during the active hear-through mode. Of course, if it is desired to mute the input audio during the active hear-through mode, this can be accomplished by simply setting the gain of $K_{eq}$ to zero, or by turning off the input audio signal path (which, in some implementations, may be the same thing).

Providing the ANR and audio playback through separate signal paths also allows the audio playback to be maintained even when the ANR circuitry is not powered at all, either because the user has turned it off or because the power supply is not available or depleted. In some examples, a secondary audio path with a different equalizing filter $K_{np}$ implemented in passive circuitry is used to deliver the input audio signal to the output transducer, bypassing the signal processor. The passive filter $K_{np}$ may be designed to reproduce, as closely as possible, the system response experienced when the system is powered, without unduly compromising sensitivity. When such a circuit is available, the signal processor or other active electronics will disconnect the passive path when the active system is powered on and replace it with the active input signal path. In some examples, the system may be configured to delay the reconnection of the input signal path as a signal to the user that the active system is now operating. The active system may also fade-in the input audio signal upon power-on, both as a signal to the user that it is operating and to provide a more gradual transition. Alternatively, the active system may be configured to make the transition from passive to active audio as smoothly as possible without dropping the audio signal. This can be accomplished by retaining the passive signal path until the active system is ready to take over, applying a set of filters to match the active signal path to the passive path, switching from the passive path to the active path, and then fading into the preferred active $K_{eq}$ filter.

When active hear-through and audio reproduction are available simultaneously, the user interface becomes more complicated than in typical ANR headphones. In one example, audio is kept on by default during active hear-through, and a momentary button which is pushed to toggle between noise reduction and hear-through modes is held in to additionally mute audio when activating hear-through. In another example, the choice of whether to mute audio on entering hear-through is a setting into which the headphone is configured according to the user's preference. In another example, a headphone configured to control a playback device, such as a smartphone, can signal the device to pause audio playback in place of muting the audio within the headphones when active hear-through is enabled. In the same example, such a headphone may be configured to activate the active hear-through mode whenever the music is paused.

Other User Interface Considerations

In general, headphones having an active hear-through feature will include some user control for activating the feature, such as a button or switch. In some examples, this user interface may take the form of more sophisticated interfaces, such as a capacitive sensor or accelerometer in the ear cup, that detects when the user touches the ear cup in a particular manner that is interpreted as calling for the active hear-through mode. In some cases, additional controls are provided. For situations where someone other than the user may need to activate a hear-through mode, such as a flight attendant needing the attention of a passenger or a teacher needing the attention of a student, an external remote control may be desirable. This could be implemented with any conventional remote control technology, but there are a few considerations due to the likely use cases of such devices.

In an aircraft, it would be assumed that multiple passengers are wearing compatible headphones, but have not coordinated their selection of these products with each other or the airline, such that the flight attendant will not have information, such as unique device IDs, needed to specify which headset is to activate its hear-through mode. In this situation, it may be desired to provide a line-of-sight remote control, such as an infrared control with a narrow beam, that must be aimed directly at a given set of headphones to activate their hear-through mode. In another situation, however, such as during pre-flight announcements or in an emergency, the flight crew may need to activate hear-through on all compatible headphones. For this situation, a number of wide-beam infrared emitters could be located throughout the aircraft, positioned to assure that each seat is covered. Another source of remote control suitable to the aircraft use case is to overlay control signals on the audio input line. In that way, any set of headphones plugged into the aircraft's entertainment audio can be signaled, and this may provide both a broadcast and seat-specific means of signaling. In the classroom, military, or business context, on the other hand, it might be the case that all the headphones were purchased or at least coordinated by a single entity, so unique device identifiers may be available, and an broadcast type of remote control, such as radio, may be used to turn active hear-through on and off at individually specified headphones.

Headphones having active circuitry generally include visible indications of their state, usually a simple on/off light. When active hear-through is provided, additional indicators are advantageous. At the simplest level, a second light may indicate to the user that the active hear-through mode is active. For situations where the user might use the active hear-through mode to communicate with others, such as a flight crew or co-workers in an office environment, additional indicators may be of value. In some examples, a light visible to others is illuminated red when ANR is active but active hear-through is not active, and the light changes to green when active hear-through is active, indicating to others that they can now talk to the user of the headphones. In some examples, the indicator light is structured so that it is only visible from a narrow range of angles, such as directly ahead of the user, so that only someone who is actually facing the user will know what state their headphones are in. This allow the wearer to still use the headphones so socially signal "do not disturb" to others they are not facing.

Automatic Hear-Through when Talking

In some examples, the feedback system is also used to automatically turn on active hear-through. When the user starts speaking, the amplitude of low-frequency pressure variations inside his ear canal is increased, as explained above, by sound pressure moving through soft tissues from the larynx to the ear canal. The feedback microphone will detect this increase. In addition to cancelling the increased pressure as part of ongoing occlusion effect compensation, the system can also use this increase in pressure amplitude to identify that the user is speaking, and therefore turn on the full active hear-through mode to provide self-naturalness of the user's voice. Band-pass filters on the feedback microphone signal, or correlation between the feedback and feed-forward microphone signals, can be used to make sure that active hear-through is switched on only in response to voice, and not to other internal pressure sources such as blood flow or body movement. When the user is speaking, the feed-forward and feedback microphones will both detect the user's voice. The feed-forward microphone will detect the air-conducted portion of the user's voice, which may cover the entire frequency range of human speech, while the feedback microphone will detect that part of the speech that is transmitted through the head, which happens to be amplified by the occlusion effect. The envelope of these signals will, therefore, be correlated within the band amplified by the occlusion effect when the user is speaking. If another person is speaking near the user, the feed-forward microphone may detect similar signals to those when the user is speaking, while any residual sound the feedback microphone detects of that speech will be significantly lower in level. By checking the correlation and the level of the signals for values consistent with the user speaking, the headphones can determine when the user is speaking, and activate the active hear-through system accordingly.

In addition to allowing the user to hear his own voice naturally, automatic activation of the active hear-through feature also allows the user to hear the response of whomever he is talking to. In such an example, the hear-through mode may be kept on for some amount of time after the user stops speaking.

An automatic active hear-through mode is also advantageous when the headphones are connected to a communications device, such as a wireless telephone, that does not provide a side tone, that is, a reproduction of the user's own voice over the near-end output. By turning on hear-through when the user is speaking or when the headset detects electronically that a call is in progress, the user hears his own voice naturally and will speak at an appropriate level into the phone. If the communications microphone is part of the same headset, a correlation between that microphone's signal and the feedback microphone's signal can be used to further confirm that the user is speaking.

Stability Protection

The active hear-through feature has the potential to introduce a new failure mode in ANR headsets. If the output transducer is acoustically coupled to the feed-forward microphone, to a greater extent than should exist under normal operation, a positive feedback loop may be created, resulting in high-frequency ringing, which may be unpleasant or off-putting to the user. This may happen, for example, if the user cups a hand over an ear when using headphones with a back cavity that is ported or open to the environment, or if the headphones are removed from the head while the active hear-through system is activated, allowing free-space coupling from the front of the output transducer to the feed-forward microphone.

This risk can be mitigated by detecting high-frequency signals in the feed-forward signal path, and activating a compressing limiter if those signals exceed a level or amplitude threshold that is indicative of such a positive feedback loop being present. Once the feedback is eliminated, the limiter may be deactivated. In some examples, the limiter is deactivated gradually, and if feedback is again detected, it is raised back to the lowest level at which feedback was not detected. In some examples, a phase locked loop monitoring the output of the feed-forward compensator $K_{ff}$ is configured to lock onto a relatively pure tone over a predefined frequency span. When the phase locked loop achieves a locking condition, this would indicate an instability which would then trigger the compressor along the feed-forward signal path. The gain at the compressor is reduced at a prescribed rate until the gain is low enough for the oscillation condition to stop. When the oscillation stops, the phase-locked loop loses the lock condition and releases the compressor, which allows the gain to recover to the normal operating value. Since the oscillation must first occur before it can be suppressed by the compressor, the user will hear a repeated chirp if the physical condition (e.g., hand position) is maintained. However, short repeated quiet chirps are much less off-putting than a sustained loud squeal.

Binaural Telepresence

Another feature made possible by the availability of active hear-through is a shared binaural telepresence. For this feature, the feed-forward microphone signals from the right and left ear cups of a first set of headphones are transmitted to a second set of headphones, which reproduces them using its own equalization filters based on the acoustics of the second set of headphones. The transmitted signals may be filtered to compensate for the specific frequency response of the feed-forward microphones, providing a more normalized signal to the remote headphones. Playing back the first set of headphones' feed-forward microphone signals in the second set of headphones allows the user of the second set of headphones to hear the environment of the first set of headphones. Such an arrangement may be reciprocal, with both sets of headphones transmitting their feed-forward microphone signals to the other. The users could either choose to each hear the other's environment, or select one environment for both of them to hear. In the latter mode, both users "share" the source user's ears, and the remote user may choose to be in full noise-cancelling mode to be immersed in the sound environment of the source user.

Such a feature can make simple communications between two people more immersive, and it may also have industrial applications, such as allowing a remote technician to hear the environment of a facility where a local co-worker or client is attempting to design or diagnose an audio system or problem. For example, an audio system engineer installing an audio system at a new auditorium may wish to consult with another system engineer located back at their home office on the sound being produced by the audio system. By both wearing such headphones, the remote engineer can here what the installer hears with sufficient clarity, due to the active hear-through filters, to give quality advice on how to tune the system.

Such a binaural telepresence system requires some system for communication, and a way to provide the microphone signals to the communication system. In one example, smart phones or tablet computers may be used. At least one set of headphones, the one providing the remote audio signals, is modified from the conventional design to provide both ears' feed-forward microphone signals as outputs to the communication device. Headset audio connections for smartphones and computers generally include only three signal paths—stereo audio to the headset, and mono microphone audio from the headset to the phone or computer. Binaural output from the headphone, in addition to any communication microphone output, may be accomplished through a non-standard application of an existing protocol, such as by making the headphones operate as a Bluetooth stereo audio source and the phone a receiver (opposite the conventional arrangement). Alternatively, additional audio signals may be provided through a wired connection with more conductors than the usual headset jack, or a proprietary wireless or wired digital protocol may be used.

However the signals are delivered to the communication device, it then transmits the pair of audio signals to the remote communication device, which provides them to the second headset. In the simplest configuration, the two audio signals may be delivered to the receiving headset as a standard stereo audio signal, but it may be more effective to deliver them separately from the normal stereo audio input to the headphones.

If the communication devices used for this system also provide video conferencing, such that the users can see each other, it may also be desirable to flip the left and right feed-forward microphone signals. This way, if one user reacts to a sound to their left, the other user hears this in their right ear, matching the direction in which the see the remote user looking in the video conference display. This reversing of signals can be done at any point in the system, but is probably most effective if it is done by the receiving communication device, as that device knows whether the user at that end is receiving the video conference signal.

Another feature made possible by providing the feed-forward microphone signals as outputs from the headphones is binaural recording with ambient naturalness on playback. That is, a binaural recording made using the raw or microphone-filtered signal from the feed-forward microphones can be played back using the $K_{eq}$ of the playback headset so that the person listening to the recording feels fully immersed in the original environment.

Other implementations are within the scope of the following claims and other claims to which the applicant may be entitled.

What is claimed is:

1. An active noise reducing headphone comprising:

an ear piece configured to couple to a wearer's ear to define an acoustic volume comprising the volume of air within the wearer's ear canal and a volume within the ear piece;

a feed-forward microphone acoustically coupled to an external environment and electrically coupled to a feed-forward active noise cancellation signal path;

a feedback microphone acoustically coupled to the acoustic volume and electrically coupled to a feedback active noise cancellation signal path;

an output transducer acoustically coupled to the acoustic volume via the volume within the ear piece and electrically coupled to both the feed-forward and feedback active noise cancellation signal paths; and a signal processor configured to apply filters and control gains of both the feed-forward and feedback active noise cancellation signal paths;

wherein the signal processor is configured to:

apply first feed-forward filters to the feed-forward signal path and apply first feedback filters to the feedback signal path during a first operating mode providing effective cancellation of ambient sound, and replace the first feed-forward filters with second feed-forward filters in the feed-forward signal path during a second operating mode providing active hear-through of ambient sounds with ambient naturalness;

and wherein the second feed-forward filters have value $K_{ht}$ selected to cause the formula $$\frac{G_{pfb}}{G_{oea}} + \frac{K_{ht} * G_{nx} * G_{ffe}}{G_{oea}}$$

to be approximately equal to a predetermined target response, where Gpfb is the transfer function from external noise to the ear, through the headphones and with the feedback active noise cancellation signal path active, Goea is the transfer function from the external noise to the ear without the headphones, Gnx is the transfer function from the external noise to the feed-forward microphone, and Gffe is the transfer function of the filtered signal to the ear, through the output transducer, with the feedback active noise cancellation signal path active, and the predetermined target response is the target hear-through insertion gain (Thtig), which is 0 dB within the hear-through pass band, and is the same as the insertion gain achieved by the first feed-forward filters outside the hear-through pass band.

2. The headphone of claim 1, wherein the second feed-forward filters cause the headphone to have a total system response at the wearer's ear that is smooth and piecewise linear.

3. The headphone of claim 2, wherein the second feed-forward filters cause the total system response to be smooth and piecewise linear in a region extending to frequencies above 3 kHz.

4. The headphone of claim 3, wherein the second feed-forward filters cause the total system response to be smooth and piecewise linear in a region extending to frequencies below 300 Hz.

5. The headphone of claim 1, wherein the difference in the overall noise reduction in speech noise between the first operating mode and the second operating mode is at least 12 dBA.

6. The headphone of claim 1, wherein the signal processor is further configured to apply second feedback filters different from the first feedback filters to the feedback signal path during the second operating mode.

7. The headphone of claim 1, wherein the feedback signal path and the ear piece in combination reduce ambient noise reaching the entrance to the ear canal by at least 8 dB at all frequencies between 100 Hz and 10 kHz.

8. The headphone of claim 1, wherein the feedback signal path is operative over a frequency range extending higher than 500 Hz.

9. The headphone of claim 1, wherein the feedback signal path is implemented in a digital signal processor and has a latency less than 250 μs.

10. The headphone of claim 1, wherein the second feed-forward filter defines non-minimum phase zeros in a transfer function characterizing the feed-forward signal path.

11. The headphone of claim 1, wherein the signal processor is further configured to:

replace the second feed-forward filters with third feed-forward filters in the feed-forward signal path during a third operating mode providing active hear-through of ambient sounds with a different total response than is provided in the second operating mode.

12. The headphone of claim 11, further comprising a user input, and wherein the signal processor is further configured to select between the first, second, or third feed-forward filters based on the user input.

13. The headphone of claim 12, wherein the user input comprises a volume control.

14. The headphone of claim 11, wherein the signal processor is configured to select between the second and third feed-forward filters automatically.

15. The headphone of claim 14, wherein the signal processor is configured to select between the second and third feed-forward filters based on a time-average measurement of the level of the ambient noise.

16. The headphone of claim 15, wherein the signal processor is configured to make the selection between the second and third feed-forward filters upon receipt of a user input calling for activation of a hear-through mode.

17. The headphone of claim 15, wherein the signal processor is configured to make the selection between the second and third feed-forward filters periodically.

18. The headphone of claim 1, wherein the signal processor is a first signal processor and the feed-forward signal path is a first feed-forward signal path, the headphone further comprising:

a second ear piece configured to couple to a wearer's second ear to define a second acoustic volume comprising the volume of air within the wearer's second ear canal and a volume within the second ear piece;

a second feed-forward microphone acoustically coupled to an external environment and electrically coupled to a second feed-forward active noise cancellation signal path;

a second feedback microphone acoustically coupled to the second acoustic volume and electrically coupled to a second feedback active noise cancellation signal path;

a second output transducer acoustically coupled to the second acoustic volume via the volume within the second ear piece and electrically coupled to both the second feed-forward and second feedback active noise cancellation signal paths; and a second signal processor configured to apply filters and control gains of both the second feed-forward and second feedback active noise cancellation signal paths;

wherein the second signal processor is configured to:

apply third feed-forward filters to the second feed-forward signal path and apply the first feedback filters to the second feedback signal path during the first operating mode of the first signal processor, and replace the third feed-forward filters with fourth feed-forward filters in the second feed-forward signal path during the second operating mode of the first signal processor.

19. The headphone of claim 18, wherein the first and second signal processors are portions of a single signal processing device.

20. The headphone of claim 18, wherein the third feed-forward filters are not identical to the first feed-forward filters.

21. The headphone of claim 18, wherein only one of the first or second signal processor applies the respective second or fourth feed-forward filters to the corresponding first or second feed-forward signal path during a third operating mode.

22. The headphone of claim 21, further comprising a user input, wherein the third operating mode is activated in response to the user input.

23. The headphone of claim 1, wherein the signal processor is further configured to apply a single-channel noise reduction filter to the first feed-forward signal path during the second operating mode.

24. The headphone of claim 1, wherein the signal processor is further configured to:

detect high-frequency signals in the feed-forward signal path, compare the amplitude of the detected high-frequency signals to a threshold indicative of a positive feedback loop, and if the amplitude of the detected high-frequency signals is higher than the threshold, activate a compressing limiter.

25. The headphone of claim 24, wherein the signal processor is configured to detect the high-frequency signals using a phase-locked loop monitoring a signal in the feed-forward signal path.

26. The headphone of claim 1, wherein the ear piece provides a volume enclosing the feed-forward microphone, and further comprising a screen covering an aperture between the volume enclosing the feed-forward microphone and the external environment.

27. The headphone of claim 26, wherein the aperture between the volume enclosing the feed-forward microphone and the external environment is at least 10 $mm^2$.

28. The headphone of claim 26, wherein the aperture between the volume enclosing the feed-forward microphone and the external environment is at least 20 $mm^2$.

29. The headphone of claim 26, wherein the screen and the feed-forward microphone are separated by a distance of at least 1.5 mm.

30. The headphone of claim 1 wherein the second feed-forward filters provide active hear-through of ambient sounds with ambient naturalness over a hear-through pass band comprising a frequency range extending at least from 300 Hz to 3 kHz.

31. An active noise reducing headphone comprising:

an ear piece configured to couple to a wearer's ear to define an acoustic volume comprising the volume of air within the wearer's ear canal and a volume within the ear piece;

a feed-forward microphone acoustically coupled to an external environment and electrically coupled to a feed-forward active noise cancellation signal path;

a feedback microphone acoustically coupled to the acoustic volume and electrically coupled to a feedback active noise cancellation signal path;

an output transducer acoustically coupled to the acoustic volume via the volume within the ear piece and electrically coupled to both the feed-forward and feedback active noise cancellation signal paths; and a signal processor configured to apply filters and control gains of both the feed-forward and feedback active noise cancellation signal paths;

wherein the signal processor is configured to:

apply first feed-forward filters to the feed-forward signal path and apply first feedback filters to the feedback signal path during a first operating mode providing effective cancellation of ambient sound, replace the first feed-forward filters with second feed-forward filters in the feed-forward signal path during a second operating mode providing active hear-through of ambient sounds with ambient naturalness, detect high-frequency signals in the feed-forward signal path, compare the amplitude of the detected high-frequency signals to a threshold indicative of a positive feedback loop, if the amplitude of the detected high-frequency signals is higher than the threshold, activate a compressing limiter;

when the amplitude of the detected high-frequency signals is no longer higher than the threshold, decrease an amount of compression applied by the limiter gradually, and if the amplitude of the detected high-frequency signals returns to a level higher than the threshold after reducing the amount of compression, increase the amount of compression to the lowest level at which the amplitude of the detected high-frequency signals remain below the threshold.

32. A method of operating an active noise reducing headphone comprising an ear piece configured to couple to a wearer's ear to define an acoustic volume comprising the volume of air within the wearer's ear canal and a volume within the ear piece;

a feed-forward microphone acoustically coupled to an external environment and electrically coupled to a feed-forward active noise cancellation signal path;

a feedback microphone acoustically coupled to the acoustic volume and electrically coupled to a feedback active noise cancellation signal path;

an output transducer acoustically coupled to the acoustic volume via the volume within the ear piece and electrically coupled to both the feed-forward and feedback active noise cancellation signal paths; and a signal processor configured to apply filters and control gains of both the feed-forward and feedback active noise cancellation signal paths, the method comprising:

in the signal processor, during a first operating mode, providing effective cancellation of ambient sound by applying first feed-forward filters to the feed-forward signal path and applying first feedback filters to the feedback signal path, and in the signal processor, during a second operating mode, providing active hear-through of ambient sounds with ambient naturalness by replacing the first feed-forward filters with second feed-forward filters and applying the second feed-forward filters to the feed-forward signal path, wherein the second feed-forward filters have value $K_{ht}$ selected to cause the formula $$\frac{G_{pfb}}{G_{oea}} + \frac{K_{ht} * G_{nx} * G_{ffe}}{G_{oea}}$$

to be approximately equal to a predetermined target response, where Gpfb is the transfer function from external noise to the ear, through the headphones and with the feedback active noise cancellation signal path active, Goea is the transfer function from the external noise to the ear without the headphones, Gnx is the transfer function from the external noise to the feed-forward microphone, and Gffe is the transfer function of the filtered signal to the ear, through the output transducer, with the feedback active noise cancellation signal path active, and the predetermined target response is the target hear-through insertion gain (Thtig), which is 0 dB within the hear-through pass band, and is the same as the insertion gain achieved by the first feed-forward filters outside the hear-through pass band.

* * * * *